(12) United States Patent
Hatanaka et al.

(10) Patent No.: US 8,053,224 B2
(45) Date of Patent: Nov. 8, 2011

(54) GLUCOSE-INDUCED INACTIVATION/DEGRADATION-RESISTANT TRANSPORTER GENE AND USE THEREOF

(75) Inventors: Haruyo Hatanaka, Osaka (JP); Fumihiko Omura, Osaka (JP)

(73) Assignee: Suntory Holdings Limited, Osaka (JP)

( * ) Notice: Subject to any disclaimer, the term of this patent is extended or adjusted under 35 U.S.C. 154(b) by 230 days.

(21) Appl. No.: 12/442,121

(22) PCT Filed: Sep. 9, 2008

(86) PCT No.: PCT/JP2008/066241
§ 371 (c)(1),
(2), (4) Date: Mar. 20, 2009

(87) PCT Pub. No.: WO2010/029612
PCT Pub. Date: Mar. 18, 2010

(65) Prior Publication Data
US 2010/0285173 A1    Nov. 11, 2010

(51) Int. Cl.
*C12N 1/19* (2006.01)
*C12N 15/63* (2006.01)
*C07H 21/04* (2006.01)

(52) U.S. Cl. .................. 435/254.2; 435/320.1; 536/23.1

(58) Field of Classification Search .................. None
See application file for complete search history.

(56) References Cited

U.S. PATENT DOCUMENTS

| 5,190,877 | A | 3/1993 | Osinga et al. | |
|---|---|---|---|---|
| 7,314,974 | B2 * | 1/2008 | Cao et al. | 800/289 |

FOREIGN PATENT DOCUMENTS

| JP | 1-153082 | 6/1989 |
|---|---|---|
| JP | 6-245750 | 9/1994 |

OTHER PUBLICATIONS

Brondijk et al. "Catabolite Inactivation of Wild-type and Mutant Maltose Transport Proteins in *Saccharomyces cerevisiae*" (1998) *J. Biol. Chem.* 273(25):15352-15357.

Medintz et al. "A PEST-like Sequence in the N-Terminal Cytoplasmic Domain of *Saccharomyces* Maltose Permease is Required for Glucose-Induced Proteolysis and Rapid Inactivation of Transport Activity" (2000) *Biochemistry* 39(15):4518-4526.
Gadura et al. "Sequences in the N-terminal Cytoplasmic Domain of *Saccharomyces cerevisiae* Maltose Permease are Required for Vacuolar Degradation but not Glucose-Induced Internalization" (2006) *Curr. Genet.* 50(2):101-114.
Kodama et al. "Improvement of Maltose Fermentation Efficiency: Constitutive Expression of *MAL* Genes in Brewing Yeasts" (1995) *J. Am. Soc. Brew. Chem.* (1995) 53(1):24-29.
Day et al. "Characterization of the Putative Maltose Tansporters Encoded by YDL247w and YJR160c" (2002) *Yeast* 19:1015-1027.
Yao et al. "Primary Structure of the Maltose-Permease-Encoding Gene of *Saccharomyces carlsbergensis*" (1989) *Gene* 79:189-197.
Cheng et al. "The Maltose Permease Encoded by the *MAL61* Gene of *Saccharomyces cerevisiae* Exhibits Both Sequence and Structural Homology to Other Sugar Transporters" (1989) *Genetics* 123:477-484.
Feuermann et al. "Sequence of a 9.8 kb Segment of Yeast Chromosome II Including the Three Genes of the *MAL3* Locus and Three Unidentified Open Reading Frames" (1995) *Yeast* 11:667-672.
U.S. Appl. No. 12/442,143 to Hatanaka et al., entitled "Glucose-Induced Inactivation/Degradation-Resistant Transporter Gene and Use Thereof" which application is the National Stage of PCT/JP2008/066237, filed Sep. 9, 2008.
U.S. Appl. No. 12/442,131 to Hatanaka et al., entitled "Hybrid Alpha-Glucoside Transporter" which application is the National Stage of PCT/JP2008/066239, filed Sep. 9, 2008.

* cited by examiner

*Primary Examiner* — Ruixiang Li
(74) *Attorney, Agent, or Firm* — Greenblum & Bernstein, PLC

(57) ABSTRACT

The present invention relates to a glucose-induced inactivation/degradation resistant transporter gene and use thereof, and more particularly to a brewery yeast having excellent assimilability of oligosaccharides (maltose, maltotriose, etc.), an alcoholic beverage produced using the yeast, and so on. In particular, the present invention relates to a glucose-induced inactivation/degradation resistant transporter such as Mal21p, etc., a gene encoding the same, a method of producing an alcoholic beverage using the same; and so on.

9 Claims, 13 Drawing Sheets

```
   1 ATGAAGGGAT TATCCTCATT AATAAACAGA AAAAAAGACA GGAACGACTC
  51 ACACTTAGAT GAGATCGAGA ATGGCGTGAA CGCTACCGAA TTCAACTCGA
 101 TAGAGATGGA GGAGCAAGGT AAGAAAAGTG ATTTGGTCT TTCCCATCAT
 151 GAGTACGGTC CAGGTCACT AATACCAAAC GATAATAATG AAGAAGTCCC
 201 CGACCTTCTC GATGAAGCTA TGCAGGACGC CAAAGAGGCA GATGAAAGTG
 251 AGAGGGGAAT GCCACTCATG ACAGCTTTGA AGACATATCC AAAAGCTGCT
 301 GCTTGGTCAC TATTAGTTTC CACAACATTG ATTCAAGAGG GTTATGACAC
 351 AGCCATTCTA GGAGCTTTCT ATGCCCTGCC TGTTTTTCAA AAAAAATATG
 401 GTTCTTTGAA TAGCAATACA GGAGATTATG AAATTTCAGT TTCTTGGCAA
 451 ATCGGTCTAT GTCTATGCTA CATGGCAGGT GAAATTGTGG GGCTACAGCT
 501 AACGGGGCCC TCCGTGGATC TTGTTGGAAA TCGTTACACA TTGATCATGG
 551 CGTTGTTCTT TTTAGCGGCT TTCATTTTCA TTCTGTATTT TTGCAAGAGT
 601 TTGGGTATGA TTGCCGTGGG ACAGGCATTG TGTGGTATGC CATGGGGTTG
 651 TTTCCAATGT TTGACCGTTT CTTATGCTTC TGAAATTTGT CCTTTGGCCC
 701 TAAGATACTA TTTGACGACT TATTCTAATT TATGTTGGAC GTTCGGTCAA
 751 CTTTTCGCTG CTGGTATTAT GAAAAATTCC CAGAACAAAT ATGCCAACTC
 801 AGAACTAGGA TATAAGCTAC CTTTTGCTTT GCAGTGGATC TGGCCCCTTC
 851 CTTTGGCGGT AGGTATTTTT TTTGCACCAG AGTCTCCATG GTGGCTGGTT
 901 AAAAAAGGAA GGATTGATCA AGCGAGGAGA TCACTTGAAA GAACATTAAG
 951 TGGTAAAGGA CCCGAGAAAG AATTACTAGT GACTATGGAA CTCGATAAAA
1001 TCAAAACTAC TATAGAAAAG GAGCAGAAAA TGTCTGATGA AGGAACTTAC
1051 TGGGATTGTG TGAAAGATGG TATTAACAGG AGAAGAACGA GAATAGCTTG
1101 TTTATGTTGG ATCGGTCAAT GCTCCTGTGG TGCATCATTA ATTGGTTATT
1151 CAACTTACTT TTATGAAAAA GCTGGTGTTA GCACTGATAC GGCTTTTACT
1201 TTCAGTATTA TCCAATATTG TCTTGGTATT GCTGCAACGT TGTATCCTG
1251 GTGGGCTTCA AAATATTGTG GCAGATTTGA CCTTTATGCT TTTGGGCTGG
1301 CTTTTCAGGC TATTATGTTC TTCATTATCG GTGGTTTAGG ATGTTCAGAC
1351 ACTCATGGCG CTAAAATGGG TAGTGGTGCT CTTCTAATGG TTGTCGCGTT
1401 CTTTTACAAC CTCGGTATTG CACCTGTTGT TTTTTGCTTA GTGTCTGAAA
1451 TGCCGTCTTC AAGGCTAAGA ACCAAAACAA TTATTTTGGC TCGTAATGCT
1501 TACAATGTGA TCCAAGTTGT AGTTACAGTT TTGATTATGT ACCAATTGAA
1551 CTCAGAGAAA TGGAATTGGG GTGCTAAATC AGGCTTTTTC TGGGGAGGAT
1601 TTTGTCTGGC CACTTTAGCT TGGGCTGTTG TCGATTTACC AGAAACCGCT
1651 GGCAGGACTT TTATTGAGAT AAATGAATTG TTTAGACTTG GTGTTCCAGC
1701 AAGAAAGTTC AAGTCGACTA AAGTCGACCC TTTTGCAGCT GCCAAAGCAG
1751 CAGCTGCAGA AATTAATGTT AAAGATCCGA AGGAAGATTT GGAAACTTCT
1801 GTGGTAGATG AAGGGCGAAA CACCTCATCT GTTGTGAACA AATGA
```

*Fig. 2*

MKGLSSLINRKKDRNDSHLDEIENGVNATEFNSIEMEEQGKKSDFGLSHH 50

EYGPGSLIPNDNNEEVPDLLDEAMQDAKEADESERGMPLMTALKTYPKAA 100

AWSLLVSTTLIQEGYDTAILGAFYALPVFQKKYGSLNSNTGDYEISVSWQ 150

IGLCLCYMAGEIVGLQLTGPSVDLVGNRYTLIMALFFLAAFIFILYFCKS 200

LGMIAVGQALCGMPWGCFQCLTVSYASEICPLALRYYLTTYSNLCWTFGQ 250

LFAAGIMKNSQNKYANSELGYKLPFALQWIWPLPLAVGIFFAPESPWWLV 300

KKGRIDQARRSLERTLSGKGPEKELLVTMELDKIKTTIEKEQKMSDEGTY 350

WDCVKDGINRRRTRIACLCWIGQCSCGASLIGYSTYFYEKAGVSTDTAFT 400

FSIIQYCLGIAATFVSWWASKYCGRFDLYAFGLAFQAIMFFIIGGLGCSD 450

THGAKMGSGALLMVVAFFYNLGIAPVVFCLVSEMPSSRLRTKTIILARNA 500

YNVIQVVVTVLIMYQLNSEKWNWGAKSGFFWGGFCLATLAWAVVDLPETA 550

GRTFIEINELFRLGVPARKFKSTKVDPFAAAKAAAAEINVKDPKEDLETS 600

VVDEGRNTSSVVNK*

*Fig. 3*

```
               1                                                  50
MAL21p   (1)   MKGLSSLINRKKDRNDSHLDEIENGVNATEFNSIEMEEQGKKSDFGLSHH
MAL31p   (1)   MKGLSSLINRKKDRNDSHLDEIENGVNATEFNSIEMEEQGKKSDFGLSHH
MAL61p   (1)   MKGLSSLINRKKDRNDSHLDEIENGVNATEFNSIEMEEQGKKSDFGLSHH
               51                                                100
MAL21p  (51)   EYGPGSLIPNDNNEEVPDLLDEAMQDAKEADESERGMPLMTALKTYPKAA
MAL31p  (51)   EYGPGSLIPNDNNEEVPDLLDEAMQDAKEADESERGMPLMTALKTYPKAA
MAL61p  (51)   EYGPGSLIPNDNNEEVPDLLDEAMQDAKEADESERGMPLMTALKTYPKAA
               101                                               150
MAL21p (101)   AWSLLVSTTLIQEGYDTAILGAFYALPVFQKKYGSLNSNTGDYEISVSWQ
MAL31p (101)   AWSLLVSTTLIQEGYDTAILGAFYALPVFQKKYGSLNSNTGDYEISVSWQ
MAL61p (101)   AWSLLVSTTLIQEGYDTAILGAFYALPVFQKKYGSLNSNTGDYEISVSWQ
               151                                               200
MAL21p (151)   IGLCLCYMAGEIVGLQITGPSVDLIGNRYTLIMALFFLAAFIFILYFCKS
MAL31p (151)   IGLCLCYMAGEIVGLQITGPSVDYMGNRYTLIMALFFLAAFIFILYFCKS
MAL61p (151)   IGLCLCYMAGEIVGLQITGPSVDYMGNRYTLIMALFFLAAFIFILYFCKS
               201                                               250
MAL21p (201)   LGMIAVGQALCGMPWGCFQCLTVSYASEICPLALRYYLTTYSNLCWIFGQ
MAL31p (201)   LGMIAVGQALCGMPWGCFQCLTVSYASEICPLALRYYLTTYSNLCWAFGQ
MAL61p (201)   LGMIAVGQALCGMPWGCFQCLTVSYASEICPLALRYYLTTYSNLCWIFGQ
               251                                               300
MAL21p (251)   LFAAGIMKNSQNKYANSELGYKLPFALQWIWPLPLAVGIFIAPESPWWLV
MAL31p (251)   LFAAGIMKNSQNKYANSELGYKLPFALQWIWPLPLAVGIFIAPESPWWLV
MAL61p (251)   LFAAGIMKNSQNKYANSELGYKLPFALQWIWPLPLAVGIFLAPESPWWLV
               301                                               350
MAL21p (301)   KKGRIDQARRSLERILSGKGPEKELLVIMELDKIKTTIEKEQKMSDEGTY
MAL31p (301)   KKGRIDQARRSLERILSGKGPEKELLVSMELDKIKTTIEKEQKMSDEGTY
MAL61p (301)   KKGRIDQARRSLERILSGKGPEKELLVSMELDKIKTTIEKEQKMSDEGTY
               351                                               400
MAL21p (351)   WDCVKDGINRRRTRIACLCWIGQCSCGASLIGYSTYFYEKAGVSTDTAFT
MAL31p (351)   WDCVKDGINRRRTRIACLCWIGQCSCGASLIGYSTYFYEKAGVSTDTAFT
MAL61p (351)   WDCVKDGINRRRTRIACLCWIGQCSCGASLIGYSTYFYEKAGVSTDTAFT
               401                                               450
MAL21p (401)   FSIIQYCLGIAATFISWWASKYCGRFDLYAFGLAFQAIMFFIIGGLGCSD
MAL31p (401)   FSIIQYCLGIAATFISWWASKYCGRFDLYAFGLAFQAIMFFIIGGLGCSD
MAL61p (401)   FSIIQYCLGIAATFISWWASKYCGRFDLYAFGLAFQAIMFFIIGGLGCSD
               451                                               500
MAL21p (451)   THGAKMGSGALLMVVAFFYNLGIAPVVFCLVSEIPSSRLRTKTIILARNA
MAL31p (451)   THGAKMGSGALLMVVAFFYNLGIAPVVFCLVSEIPSSRLRTKTIILARNA
MAL61p (451)   THGAKMGSGALLMVVAFFYNLGIAPVVFCLVSEIPSSRLRTKTIILARNA
               501                                               550
MAL21p (501)   YNVIQVVVTVLIMYQLNSEKWNWGAKSGFFWGGFCLATLAWAVVDLPETA
MAL31p (501)   YNVIQVVVTVLIMYQLNSEKWNWGAKSGFFWGGFCLATLAWAVVDLPETA
MAL61p (501)   YNVIQVVVTVLIMYQLNSEKWNWGAKSGFFWGGFCLATLAWAVVDLPETA
               551                                               600
MAL21p (551)   GRTFIEINELFRLGVPARKFKSTKVDPFAAAKAAAAEINVKDPKEDLETS
MAL31p (551)   GRTFIEINELFRLGVPARKFKSTKVDPFAAAKAAAAEINVKDPKEDLETS
MAL61p (551)   GRTFIEINELFRLGVPARKFKSTKVDPFAAAKAAAAEINVKDPKEDLETS
               601           615
MAL21p (601)   VVDEGRNTSVVNK-
MAL31p (601)   VVDEGRNTSVVNK-
MAL61p (601)   VVDEGRSTPSVVNK-
```

*Fig. 4-1*

```
                1                                               50
MAL21    (1)    ATGAAGGGATTATCCTCATTAATAAACAGAAAAAAAGACAGGAACGACTC
MAL31    (1)    ATGAAGGGATTATCCTCATTAATAAACAGAAAAAAAGACAGGAACGACTC
MAL61    (1)    ATGAAGGGATTATCCTCATTAATAAACAGAAAAAAAGACAGGAACGACTC
                51                                              100
MAL21    (51)   ACACTTAGATGAGATCGAGAATGGCGTGAACGCTACCGAATTCAACTCGA
MAL31    (51)   ACACTTAGATGAGATCGAGAATGGCGTGAACGCTACCGAATTCAACTCGA
MAL61    (51)   ACACTTAGATGAGATCGAGAATGGCGTGAACGCTACCGAATTCAACTCGA
                101                                             150
MAL21    (101)  TAGAGATGGAGGAGCAAGGTAAGAAAAGTGATTTTGGTCTTTCCCATCAT
MAL31    (101)  TAGAGATGGAGGAGCAAGGTAAGAAAAGTGATTTTGATCTTTCCCATCTT
MAL61    (101)  TAGAGATGGAGGAGCAAGGTAAGAAAAGTGATTTTGATCTTTCCCATCTT
                151                                             200
MAL21    (151)  GAGTACGGTCCAGGTTCACTAATACCAAACGATAATAATGAAGAAGTCCC
MAL31    (151)  GAGTACGGTCCAGGTTCACTAATACCAAACGATAATAATGAAGAAGTCCC
MAL61    (151)  GAGTACGGTCCAGGTTCACTAATACCAAACGATAATAATGAAGAAGTCCC
                201                                             250
MAL21    (201)  CGACCTTCTCGATGAAGCTATGCAGGACGCCAAAGAGGCAGATGAAAGTG
MAL31    (201)  CGACCTTCTCGATGAAGCTATGCAGGACGCCAAAGAGGCAGATGAAAGTG
MAL61    (201)  CGACCTTCTCGATGAAGCTATGCAGGACGCCAAAGAGGCAGATGAAAGTG
                251                                             300
MAL21    (251)  AGAGGGGAATGCCACTCATGACAGCTTTGAAGACATATCCAAAAGCTGCT
MAL31    (251)  AGAGGGGAATGCCACTCATGACAGCTTTGAAGACATATCCAAAAGCTGCT
MAL61    (251)  AGAGGGGAATGCCACTCATGACAGCTTTGAAGACATATCCAAAAGCTGCT
                301                                             350
MAL21    (301)  GCTTGGTCACTATTAGTTTCCACAACATTGATTCAAGAGGGTTATGACAC
MAL31    (301)  GCTTGGTCACTATTAGTTTCCACAACATTGATTCAAGAGGGTTATGACAC
MAL61    (301)  GCTTGGTCACTATTAGTTTCCACAACATTGATTCAAGAGGGTTATGACAC
                351                                             400
MAL21    (351)  AGCCATTCTAGGAGCTTTCTATGCCCTGCCTGTTTTTCAAAAAAAATATG
MAL31    (351)  AGCCATTCTAGGAGCTTTCTATGCCCTGCCTGTTTTTCAAAAAAAATATG
MAL61    (351)  AGCCATTCTAGGAGCTTTCTATGCCCTGCCTGTTTTTCAAAAAAAATATG
                401                                             450
MAL21    (401)  GTTCTTTGAATAGCAATACAGGAGATTATGAAATTTCAGTTTCTTGGCAA
MAL31    (401)  GTTCTTTGAATAGCAATACAGGAGATTATGAAATTTCAGTTTCCTGGCAA
MAL61    (401)  GTTCTTTGAATAGCAATACAGGAGATTATGAAATTTCAGTTTCCTGGCAA
                451                                             500
MAL21    (451)  ATCGGTCTATGTCTATGCTACATGGCAGGTGAAATTGTGGGGCTACAGCT
MAL31    (451)  ATCGGTCTATGTCTATGCTACATGGCAGGTGAGATTGTCGGTTTGCAAAT
MAL61    (451)  ATCGGTCTATGTCTATGCTACATGGCAGGTGAGATTGTCGGTTTGCAAGT
                501                                             550
MAL21    (501)  AACGGGGCCCTCCGTGGATCTTGTTGGAAATCGTTACACATTGATCATGG
MAL31    (501)  GACTGGGCCTTCTGTAGATTACATGGGCAACCGTTACACTCTGATCATGG
MAL61    (501)  GACTGGGCCTTCTGTAGATTACATGGGCAACCGTTACACTCTGATCATGG
                551                                             600
MAL21    (551)  CGTTGTTCTTTTTAGCGGCTTTCATTTTCATTCTGTATTTTTGCAAGAGT
MAL31    (551)  CGTTGTTCTTTTTAGCGGCTTTCATTTTCATTCTGTATTTTTGCAAGAGT
MAL61    (551)  CGTTGTTCTTTTTAGCGGCTTTCATTTTCATTCTGTATTTTTGCAAGAGT
                601                                             650
MAL21    (601)  TTGGGTATGATTGCCGTGGGACAGGCATTGTGTGGTATGCCATGGGGTTG
MAL31    (601)  TTGGGTATGATTGCCGTGGGACAGGCATTGTGTGGTATGCCATGGGGTTG
MAL61    (601)  TTGGGTATGATTGCCGTGGGACAGGCATTGTGTGGTATGCCATGGGGTTG
```

*Fig. 4-2*

```
            651                                                       700
MAL21  (651) TTTCCAATGTTTGACCGTTTCTTATGCTTCTGAAATTTGTCCTTTGGCCC
MAL31  (651) TTTCCAATGTTTGACCGTTTCTTATGCTTCTGAAATTTGTCCTTTGGCCC
MAL61  (651) TTTCCAATGTTTGACCGTTTCTTATGCTTCTGAAATTTGTCCTTTGGCCC
            701                                                       750
MAL21  (701) TAAGATACTATTTGACGACTTATTCTAATTTATGTTGGACGTTCGGTCAA
MAL31  (701) TAAGATACTATTTGACGACTTATTCTAATTTATGTTGGCGTTCGGTCAA
MAL61  (701) TAAGATACTATTTGACGACTTATTCTAATTTATGTTGGACGTTCGGTCAA
            751                                                       800
MAL21  (751) CTTTTCGCTGCTGGTATTATGAAAAATTCCCAGAACAAATATGCCAACTC
MAL31  (751) CTTTTCGCTGCTGGTATTATGAAAAATTCCCAGAACAAATATGCCAACTC
MAL61  (751) CTTTTCGCTGCTGGTATTATGAAAAATTCCCAGAACAAATATGCCAACTC
            801                                                       850
MAL21  (801) AGAACTAGGATATAAGCTACCTTTTGCTTTGCAGTGGATCTGGCCCCTTC
MAL31  (801) AGAACTAGGATATAAGCTACCTTTTGCTTTGCAGTGGATCTGGCCCCTTC
MAL61  (801) AGAACTAGGATATAAGCTACCTTTTGCTTTGCAGTGGATCTGGCCCCTTC
            851                                                       900
MAL21  (851) CTTTGGCGGTAGGTATTTTTTTTGCACCAGAGTCTCCATGGTGGCTGGTT
MAL31  (851) CTTTGGCGGTAGGTATTTTTTTTGCACCAGAGTCTCCATGGTGGCTGGTT
MAL61  (851) CTTTGGCGGTAGGTATTTTTTTTGGCACCAGAGTCTCCATGGTGGCTGGTT
            901                                                       950
MAL21  (901) AAAAAAGGAAGGATTGATCAAGCGAGGAGATCACTTGAAAGAACATTAAG
MAL31  (901) AAAAAAGGAAGGATTGATCAAGCGAGGAGATCACTTGAAAGAACATTAAG
MAL61  (901) AAAAAAGGAAGGATTGATCAGGCGAGGAGATCACTTGAAAGAATATTAAG
            951                                                       1000
MAL21  (951) TGGTAAAGGACCCGAGAAAGAATTACTAGTGACTATGGAACTCGATAAAA
MAL31  (951) TGGTAAAGGACCCGAGAAAGAATTACTAGTGAGTATGGAACTCGATAAAA
MAL61  (951) TGGTAAAGGACCCGAGAAAGAATTACTAGTGAGTATGGAACTCGATAAAA
            1001                                                      1050
MAL21 (1001) TCAAAACTACTATAGAAAAGGAGCAGAAAATGTCTGATGAAGGAACTTAC
MAL31 (1001) TCAAAACTACTATAGAAAAGGAGCAGAAAATGTCTGATGAAGGAACTTAC
MAL61 (1001) TCAAAACTACTATAGAAAAGGAGCAGAAAATGTCTGATGAAGGAACTTAC
            1051                                                      1100
MAL21 (1051) TGGGATTGTGTGAAAGATGGTATTAACAGGAGAAGAACGAGAATAGCTTG
MAL31 (1051) TGGGATTGTGTGAAAGATGGTATTAACAGGAGAAGAACGAGAATAGCTTG
MAL61 (1051) TGGGATTGTGTGAAAGATGGTATTAACAGGAGAAGAACGAGAATAGCTTG
            1101                                                      1150
MAL21 (1101) TTTATGTTGGATCGGTCAATGCTCCTGTGGTGCATCATTAATTGGTTATT
MAL31 (1101) TTTATGTTGGATCGGTCAATGCTCCTGTGGTGCATCATTAATTGGTTATT
MAL61 (1101) TTTATGTTGGATCGGTCAATGCTCCTGTGGTGCATCATTAATTGGTTATT
            1151                                                      1200
MAL21 (1151) CAACTTACTTTTATGAAAAAGCTGGTGTTAGCACTGATACGGCTTTTACT
MAL31 (1151) CAACTTACTTTTATGAAAAAGCTGGTGTTAGCACTGATACGGCTTTTACT
MAL61 (1151) CAACTTACTTTTATGAAAAAGCTGGTGTTAGCACTGATACGGCTTTTACT
            1201                                                      1250
MAL21 (1201) TTCAGTATTATCCAATATTGTCTTGGTATTGCTGCAACGTTTGTATCCTG
MAL31 (1201) TTCAGTATTATCCAATATTGTCTTGGTATTGCTGCAACGTTTATATCCTG
MAL61 (1201) TTCAGTATTATCCAATATTGTCTTGGTATTGCTGCAACGTTTGTATCCTG
            1251                                                      1300
MAL21 (1251) GTGGGCTTCAAAATATTGTGGCAGATTTGACCTTTATGCTTTTGGGCTGG
MAL31 (1251) GTGGGCTTCAAAATATTGTGGCAGATTTGACCTTTATGCTTTTGGGCTGG
MAL61 (1251) GTGGGCTTCAAAATATTGTGGCAGATTTGACCTTTATGCTTTTGGGCTGG
```

*Fig. 4-3*

```
              1301                                               1350
MAL21 (1301)  CTTTTCAGGCTATTATGTTCTTCATTATCGGTGGTTTAGGATGTTCAGAC
MAL31 (1301)  CTTTTCAGGCTATTATGTTCTTCATTATCGGTGGTTTAGGATGTTCAGAC
MAL61 (1301)  CTTTTCAGGCTATTATGTTCTTCATTATCGGTGGTTTAGGATGTTCAGAC
              1351                                               1400
MAL21 (1351)  ACTCATGGCGCTAAAATGGGTAGTGGTGCTCTTCTAATGGTTGTCGCGTT
MAL31 (1351)  ACTCATGGCGCTAAAATGGGTAGTGGTGCTCTTCTAATGGTTGTCGCGTT
MAL61 (1351)  ACTCATGGCGCTAAAATGGGTAGTGGTGCTCTTCTAATGGTTGTCGCGTT
              1401                                               1450
MAL21 (1401)  CTTTTACAACCTCGGTATTGCACCTGTTGTTTTTGCTTAGTGTCTGAAA
MAL31 (1401)  CTTTTACAACCTCGGTATTGCACCTGTTGTTTTTGCTTAGTGTCTGAAA
MAL61 (1401)  CTTTTACAACCTCGGTATTGCACCTGTTGTTTTTGCTTAGTGTCTGAAA
              1451                                               1500
MAL21 (1451)  TGCCGTCTTCAAGGCTAAGAACCAAAACAATTATTTTGGCTCGTAATGCT
MAL31 (1451)  TACCGTCTTCAAGGCTAAGAACCAAAACAATTATTTTGGCTCGTAATGCT
MAL61 (1451)  TGCCGTCTTCAAGGCTAAGAACCAAAACAATTATTTTGGCTCGTAATGCT
              1501                                               1550
MAL21 (1501)  TACAATGTGATCCAAGTTGTAGTTACAGTTTTGATTATGTACCAATTGAA
MAL31 (1501)  TACAATGTGATCCAAGTTGTAGTTACAGTTTTGATCATGTACCAATTGAA
MAL61 (1501)  TACAATGTGATCCAAGTTGTAGTTACAGTTTTGATCATGTACCAATTGAA
              1551                                               1600
MAL21 (1551)  CTCAGAGAAATGGAATTGGGGTGCTAAATCAGGCTTTTTCTGGGGAGGAT
MAL31 (1551)  CTCAGAGAAATGGAATTGGGGTGCTAAATCAGGCTTTTTCTGGGGAGGAT
MAL61 (1551)  CTCAGAGAAATGGAATTGGGGTGCTAAATCAGGCTTTTTCTGGGGAGGAT
              1601                                               1650
MAL21 (1601)  TTTGTCTGGCCACTTTAGCTTGGGCTGTTGTCGATTTACCAGAAACCGCT
MAL31 (1601)  TTTGTCTGGCCACTTTAGCTTGGGCTGTTGTCGATTTACCAGAAACCGCT
MAL61 (1601)  TTTGTCTGGCCACTTTAGCTTGGGCTGTTGTCGATTTACCAGAAACCGCT
              1651                                               1700
MAL21 (1651)  GGCAGGACTTTTATTGAGATAAATGAATTGTTTAGACTTGGTGTTCCAGC
MAL31 (1651)  GGCAGGACTTTTATTGAGATAAATGAATTGTTTAGACTTGGTGTTCCAGC
MAL61 (1651)  GGCAGGACTTTTATTGAGATAAATGAATTGTTTAGACTTGGTGTTCCAGC
              1701                                               1750
MAL21 (1701)  AAGAAAGTTCAAGTCGACTAAAGTCGACCCTTTTGCAGCTGCCAAAGCAG
MAL31 (1701)  AAGAAAGTTCAAGTCGACTAAAGTCGACCCTTTTGCAGCTGCCAAAGCAG
MAL61 (1701)  AAGAAAGTTCAAGTCGACTAAAGTCGACCCTTTTGCAGCTGCCAAAGCAG
              1751                                               1800
MAL21 (1751)  CAGCTGCAGAAATTAATGTTAAAGATCCGAAGGAAGATTTGGAAACTTCT
MAL31 (1751)  CAGCTGCAGAAATTAATGTTAAAGATCCGAAGGAAGATTTGGAAACTTCT
MAL61 (1751)  CAGCTGCAGAAATTAATGTTAAAGATCCGAAGGAAGATTTGGAAACTTCT
              1801                                          1845
MAL21 (1801)  GTGGTAGATGAAGGGCGAAACACCCCATCTGTTGTGAACAAATGA
MAL31 (1801)  GTGGTAGATGAAGGGCGAAACACCCCATCTGTTGTGAACAAATGA
MAL61 (1801)  GTGGTAGATGAAGGGCGAAGCACCCCATCTGTTGTGAACAAATGA
```

*Fig. 4-4*

SEQUENCE LISTING

```
<160> NUMBER OF SEQ ID NOS: 11

<210> SEQ ID NO 1
<211> LENGTH: 1842
<212> TYPE: DNA
<213> ORGANISM: Saccharomyces cerevisiae
<220> FEATURE:
<221> NAME/KEY: CDS
<222> LOCATION: (1)..(1842)
<223> OTHER INFORMATION: Mal21 Transporter Protein

<400> SEQUENCE: 1 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
                20                  25                  30 tcg ata gag atg gag gag caa ggt aag aaa agt gat ttt ggt ctt tcc     144
Ser Ile Glu Met Glu Glu Gln Gly Lys Lys Ser Asp Phe Gly Leu Ser
            35                  40                  45 cat cat gag tac ggt cca ggt tca cta ata cca aac gat aat aat gaa     192
His His Glu Tyr Gly Pro Gly Ser Leu Ile Pro Asn Asp Asn Asn Glu
        50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80
```

```
gat gaa agt gag agg gga atg cca ctc atg aca gct ttg aag aca tat      288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa      336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt      384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa      432
Phe Gln Lys Lys Tyr Gly Ser Leu Asn Ser Asn Thr Gly Asp Tyr Glu
    130                 135                 140 att tca gtt tct tgg caa atc ggt cta tgt cta tgc tac atg gca ggt      480
Ile Ser Val Ser Trp Gln Ile Gly Leu Cys Leu Cys Tyr Met Ala Gly
145                 150                 155                 160 gaa att gtg ggg cta cag cta acg ggg ccc tcc gtg gat ctt gtt gga      528
Glu Ile Val Gly Leu Gln Leu Thr Gly Pro Ser Val Asp Leu Val Gly
                165                 170                 175 aat cgt tac aca ttg atc atg gcg ttg ttc ttt tta gcg gct ttc att      576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag      624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct      672
Ala Leu Cys Gly Met Pro Trp Gly Cys Phe Gln Cys Leu Thr Val Ser
    210                 215                 220 tat gct tct gaa att tgt cct ttg gcc cta aga tac tat ttg acg act      720
Tyr Ala Ser Glu Ile Cys Pro Leu Ala Leu Arg Tyr Tyr Leu Thr Thr
225                 230                 235                 240 tat tct aat tta tgt tgg acg ttc ggt caa ctt ttc gct gct ggt att      768
Tyr Ser Asn Leu Cys Trp Thr Phe Gly Gln Leu Phe Ala Ala Gly Ile
                245                 250                 255 atg aaa aat tcc cag aac aaa tat gcc aac tca gaa cta gga tat aag      816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt      864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg      912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga      960
Ile Asp Gln Ala Arg Arg Ser Leu Glu Arg Thr Leu Ser Gly Lys Gly
305                 310                 315                 320 ccc gag aaa gaa tta cta gtg act atg gaa ctc gat aaa atc aaa act     1008
Pro Glu Lys Glu Leu Leu Val Thr Met Glu Leu Asp Lys Ile Lys Thr
                325                 330                 335 act ata gaa aag gag cag aaa atg tct gat gaa gga act tac tgg gat     1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta     1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca     1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act     1200
Thr Tyr Phe Tyr Glu Lys Ala Gly Val Ser Thr Asp Thr Ala Phe Thr
385                 390                 395                 400
```

| | | | | | | | | | | | | | | | | |
|---|---|---|---|---|---|---|---|---|---|---|---|---|---|---|---|---|
| ttc | agt | att | atc | caa | tat | tgt | ctt | ggt | att | gct | gca | acg | ttt | gta | tcc | 1248 |
| Phe | Ser | Ile | Ile | Gln | Tyr | Cys | Leu | Gly | Ile | Ala | Ala | Thr | Phe | Val | Ser | |
| | | 405 | | | | | 410 | | | | | 415 | | | | |
| tgg | tgg | gct | tca | aaa | tat | tgt | ggc | aga | ttt | gac | ctt | tat | gct | ttt | ggg | 1296 |
| Trp | Trp | Ala | Ser | Lys | Tyr | Cys | Gly | Arg | Phe | Asp | Leu | Tyr | Ala | Phe | Gly | |
| | | 420 | | | | | 425 | | | | | 430 | | | | |
| ctg | gct | ttt | cag | gct | att | atg | ttc | ttc | att | atc | ggt | ggt | tta | gga | tgt | 1344 |
| Leu | Ala | Phe | Gln | Ala | Ile | Met | Phe | Phe | Ile | Ile | Gly | Gly | Leu | Gly | Cys | |
| | | 435 | | | | | 440 | | | | | 445 | | | | |
| tca | gac | act | cat | ggc | gct | aaa | atg | ggt | agt | ggt | gct | ctt | cta | atg | gtt | 1392 |
| Ser | Asp | Thr | His | Gly | Ala | Lys | Met | Gly | Ser | Gly | Ala | Leu | Leu | Met | Val | |
| | 450 | | | | | 455 | | | | | 460 | | | | | |
| gtc | gcg | ttc | ttt | tac | aac | ctc | ggt | att | gca | cct | gtt | gtt | ttt | tgc | tta | 1440 |
| Val | Ala | Phe | Phe | Tyr | Asn | Leu | Gly | Ile | Ala | Pro | Val | Val | Phe | Cys | Leu | |
| 465 | | | | | 470 | | | | | 475 | | | | | 480 | |
| gtg | tct | gaa | atg | ccg | tct | tca | agg | cta | aga | acc | aaa | aca | att | att | ttg | 1488 |
| Val | Ser | Glu | Met | Pro | Ser | Ser | Arg | Leu | Arg | Thr | Lys | Thr | Ile | Ile | Leu | |
| | | | | 485 | | | | | 490 | | | | | 495 | | |
| gct | cgt | aat | gct | tac | aat | gtg | atc | caa | gtt | gta | gtt | aca | gtt | ttg | att | 1536 |
| Ala | Arg | Asn | Ala | Tyr | Asn | Val | Ile | Gln | Val | Val | Val | Thr | Val | Leu | Ile | |
| | | | 500 | | | | | 505 | | | | | 510 | | | |
| atg | tac | caa | ttg | aac | tca | gag | aaa | tgg | aat | tgg | ggt | gct | aaa | tca | ggc | 1584 |
| Met | Tyr | Gln | Leu | Asn | Ser | Glu | Lys | Trp | Asn | Trp | Gly | Ala | Lys | Ser | Gly | |
| | | 515 | | | | | 520 | | | | | 525 | | | | |
| ttt | ttc | tgg | gga | gga | ttt | tgt | ctg | gcc | act | tta | gct | tgg | gct | gtt | gtc | 1632 |
| Phe | Phe | Trp | Gly | Gly | Phe | Cys | Leu | Ala | Thr | Leu | Ala | Trp | Ala | Val | Val | |
| | | 530 | | | | | 535 | | | | | 540 | | | | |
| gat | tta | cca | gaa | acc | gct | ggc | agg | act | ttt | att | gag | ata | aat | gaa | ttg | 1680 |
| Asp | Leu | Pro | Glu | Thr | Ala | Gly | Arg | Thr | Phe | Ile | Glu | Ile | Asn | Glu | Leu | |
| 545 | | | | | 550 | | | | | 555 | | | | | 560 | |
| ttt | aga | ctt | ggt | gtt | cca | gca | aga | aag | ttc | aag | tcg | act | aaa | gtc | gac | 1728 |
| Phe | Arg | Leu | Gly | Val | Pro | Ala | Arg | Lys | Phe | Lys | Ser | Thr | Lys | Val | Asp | |
| | | | | 565 | | | | | 570 | | | | | 575 | | |
| cct | ttt | gca | gct | gcc | aaa | gca | gca | gct | gca | gaa | att | aat | gtt | aaa | gat | 1776 |
| Pro | Phe | Ala | Ala | Ala | Lys | Ala | Ala | Ala | Ala | Glu | Ile | Asn | Val | Lys | Asp | |
| | | | 580 | | | | | 585 | | | | | 590 | | | |
| ccg | aag | gaa | gat | ttg | gaa | act | tct | gtg | gta | gat | gaa | ggg | cga | aac | acc | 1824 |
| Pro | Lys | Glu | Asp | Leu | Glu | Thr | Ser | Val | Val | Asp | Glu | Gly | Arg | Asn | Thr | |
| | | 595 | | | | | 600 | | | | | 605 | | | | |
| tca | tct | gtt | gtg | aac | aaa | | | | | | | | | | | 1842 |
| Ser | Ser | Val | Val | Asn | Lys | | | | | | | | | | | |
| | 610 | | | | | | | | | | | | | | | |

<210> SEQ ID NO 2
<211> LENGTH: 614
<212> TYPE: PRT
<213> ORGANISM: Saccharomyces cerevisiae

<400> SEQUENCE: 2

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Gly Leu Ser
        35                  40                  45

His His Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

```
Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
            115                 120                 125

Phe Gln Lys Lys Tyr Gly Ser Leu Asn Ser Asn Thr Gly Asp Tyr Glu
        130                 135                 140

Ile Ser Val Ser Trp Gln Ile Gly Leu Cys Leu Cys Tyr Met Ala Gly
145                 150                 155                 160

Glu Ile Val Gly Leu Gln Leu Thr Gly Pro Ser Val Asp Leu Val Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
        275                 280                 285

Ile Phe Phe Ala Pro Glu Ser Pro Trp Trp Leu Val Lys Lys Gly Arg
    290                 295                 300

Ile Asp Gln Ala Arg Arg Ser Leu Glu Arg Thr Leu Ser Gly Lys Gly
305                 310                 315                 320

Pro Glu Lys Glu Leu Leu Val Thr Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Arg Thr Arg Ile Ala Cys Leu
        355                 360                 365

Cys Trp Ile Gly Gln Cys Ser Cys Gly Ala Ser Leu Ile Gly Tyr Ser
    370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Val Ser
                405                 410                 415

Trp Trp Ala Ser Lys Tyr Cys Gly Arg Phe Asp Leu Tyr Ala Phe Gly
            420                 425                 430

Leu Ala Phe Gln Ala Ile Met Phe Phe Ile Ile Gly Gly Leu Gly Cys
        435                 440                 445

Ser Asp Thr His Gly Ala Lys Met Gly Ser Gly Ala Leu Leu Met Val
    450                 455                 460

Val Ala Phe Phe Tyr Asn Leu Gly Ile Ala Pro Val Val Phe Cys Leu
465                 470                 475                 480

Val Ser Glu Met Pro Ser Ser Arg Leu Arg Thr Lys Thr Ile Ile Leu
                485                 490                 495

Ala Arg Asn Ala Tyr Asn Val Ile Gln Val Val Val Thr Val Leu Ile
            500                 505                 510
```

-continued

```
Met Tyr Gln Leu Asn Ser Glu Lys Trp Asn Trp Gly Ala Lys Ser Gly
            515                 520                 525

Phe Phe Trp Gly Gly Phe Cys Leu Ala Thr Leu Ala Trp Ala Val Val
        530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Ala Glu Ile Asn Val Lys Asp
            580                 585                 590

Pro Lys Glu Asp Leu Glu Thr Ser Val Val Asp Gly Arg Asn Thr
        595                 600                 605

Ser Ser Val Val Asn Lys
        610

<210> SEQ ID NO 3
<211> LENGTH: 1842
<212> TYPE: DNA
<213> ORGANISM: Saccharomyces cerevisiae
<220> FEATURE:
<221> NAME/KEY: CDS
<222> LOCATION: (1)..(1842)
<223> OTHER INFORMATION: Mal31 Transporter Protein

<400> SEQUENCE: 3 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
            20                  25                  30 tcg ata gag atg gag gag caa ggt aag aaa agt gat ttt gat ctt tcc     144
Ser Ile Glu Met Glu Glu Gln Gly Lys Lys Ser Asp Phe Asp Leu Ser
        35                  40                  45 cat ctt gag tac ggt cca ggt tca cta ata cca aac gat aat aat gaa     192
His Leu Glu Tyr Gly Pro Gly Ser Leu Ile Pro Asn Asp Asn Asn Glu
    50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt     384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140 att tca gtt tcc tgg caa atc ggt cta tgt cta tgc tac atg gca ggt     480
Ile Ser Val Ser Trp Gln Ile Gly Leu Cys Leu Cys Tyr Met Ala Gly
145                 150                 155                 160 gag att gtc ggt ttg caa atg act ggg cct tct gta gat tac atg ggc     528
Glu Ile Val Gly Leu Gln Met Thr Gly Pro Ser Val Asp Tyr Met Gly
                165                 170                 175 aac cgt tac act ctg atc atg gcg ttg ttc ttt tta gcg gct ttc att     576
Asn Arg Tyr Thr Leu Ile Met Ala Leu Phe Phe Leu Ala Ala Phe Ile
```

```
                 180                 185                 190
ttc att ctg tat ttt tgc aag agt ttg ggt atg att gcc gtg gga cag     624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct     672
Ala Leu Cys Gly Met Pro Trp Gly Cys Phe Gln Cys Leu Thr Val Ser
210                 215                 220 tat gct tct gaa att tgt cct ttg gcc cta aga tac tat ttg acg act     720
Tyr Ala Ser Glu Ile Cys Pro Leu Ala Leu Arg Tyr Tyr Leu Thr Thr
225                 230                 235                 240 tat tct aat tta tgt tgg gcg ttc ggt caa ctt ttc gct gct ggt att     768
Tyr Ser Asn Leu Cys Trp Ala Phe Gly Gln Leu Phe Ala Ala Gly Ile
                245                 250                 255 atg aaa aat tcc cag aac aaa tat gcc aac tca gaa cta gga tat aag     816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt     864
Leu Pro Phe Ala Leu Gln Trp Ile Trp Pro Leu Pro Leu Ala Val Gly
        275                 280                 285 att ttt ttt gca cca gag tct cca tgg tgg ctg gtt aaa aaa gga agg     912
Ile Phe Phe Ala Pro Glu Ser Pro Trp Trp Leu Val Lys Lys Gly Arg
    290                 295                 300 att gat caa gcg agg aga tca ctt gaa aga aca tta agt ggt aaa gga     960
Ile Asp Gln Ala Arg Arg Ser Leu Glu Arg Thr Leu Ser Gly Lys Gly
305                 310                 315                 320 ccc gag aaa gaa tta cta gtg agt atg gaa ctc gat aaa atc aaa act    1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat    1056
Thr Ile Glu Lys Glu Gln Lys Met Ser Asp Glu Gly Thr Tyr Trp Asp
            340                 345                 350 tgt gtg aaa gat ggt att aac agg aga aga acg aga ata gct tgt tta    1104
Cys Val Lys Asp Gly Ile Asn Arg Arg Arg Thr Arg Ile Ala Cys Leu
        355                 360                 365 tgt tgg atc ggt caa tgc tcc tgt ggt gca tca tta att ggt tat tca    1152
Cys Trp Ile Gly Gln Cys Ser Cys Gly Ala Ser Leu Ile Gly Tyr Ser
    370                 375                 380 act tac ttt tat gaa aaa gct ggt gtt agc act gat acg gct ttt act    1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt ata tcc    1248
Phe Ser Ile Ile Gln Tyr Cys Leu Gly Ile Ala Ala Thr Phe Ile Ser
                405                 410                 415 tgg tgg gct tca aaa tat tgt ggc aga ttt gac ctt tat gct ttt ggg    1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt    1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt    1392
Ser Asp Thr His Gly Ala Lys Met Gly Ser Gly Ala Leu Leu Met Val
    450                 455                 460 gtc gcg ttc ttt tac aac ctc ggt att gca cct gtt gtt ttt tgc tta    1440
Val Ala Phe Phe Tyr Asn Leu Gly Ile Ala Pro Val Val Phe Cys Leu
465                 470                 475                 480 gtg tct gaa ata ccg tct tca agg cta aga acc aaa aca att att ttg    1488
Val Ser Glu Ile Pro Ser Ser Arg Leu Arg Thr Lys Thr Ile Ile Leu
                485                 490                 495 gct cgt aat gct tac aat gtg atc caa gtt gta gtt aca gtt ttg atc    1536
Ala Arg Asn Ala Tyr Asn Val Ile Gln Val Val Val Thr Val Leu Ile
```

```
                       500                 505                 510
atg tac caa ttg aac tca gag aaa tgg aat tgg ggt gct aaa tca ggc    1584
Met Tyr Gln Leu Asn Ser Glu Lys Trp Asn Trp Gly Ala Lys Ser Gly
    515                 520                 525 ttt ttc tgg gga gga ttt tgt ctg gcc act tta gct tgg gct gtt gtc    1632
Phe Phe Trp Gly Gly Phe Cys Leu Ala Thr Leu Ala Trp Ala Val Val
530                 535                 540 gat tta cca gaa acc gct ggc agg act ttt att gag ata aat gaa ttg    1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac    1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat    1776
Pro Phe Ala Ala Ala Lys Ala Ala Ala Ala Glu Ile Asn Val Lys Asp
            580                 585                 590 ccg aag gaa gat ttg gaa act tct gtg gta gat gaa ggg cga aac acc    1824
Pro Lys Glu Asp Leu Glu Thr Ser Val Val Asp Glu Gly Arg Asn Thr
        595                 600                 605 tca tct gtt gtg aac aaa                                            1842
Ser Ser Val Val Asn Lys
    610

<210> SEQ ID NO 4
<211> LENGTH: 614
<212> TYPE: PRT
<213> ORGANISM: Saccharomyces cerevisiae

<400> SEQUENCE: 4

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His Leu Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Met Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220
```

| | | | | | | | | | | | | | | |
|---|---|---|---|---|---|---|---|---|---|---|---|---|---|---|
|Tyr|Ala|Ser|Glu|Ile|Cys|Pro|Leu|Ala|Leu|Arg|Tyr|Leu|Thr|Thr|
|225| | | | |230| | | | |235| | | |240|
|Tyr|Ser|Asn|Leu|Cys|Trp|Ala|Phe|Gly|Gln|Leu|Phe|Ala|Ala|Gly|Ile|
| | | | |245| | | | |250| | | | |255|
|Met|Lys|Asn|Ser|Gln|Asn|Lys|Tyr|Ala|Asn|Ser|Glu|Leu|Gly|Tyr|Lys|
| | | |260| | | | |265| | | | |270| | |
|Leu|Pro|Phe|Ala|Leu|Gln|Trp|Ile|Trp|Pro|Leu|Pro|Leu|Ala|Val|Gly|
| | |275| | | | |280| | | | |285| | | |
|Ile|Phe|Phe|Ala|Pro|Glu|Ser|Pro|Trp|Trp|Leu|Val|Lys|Lys|Gly|Arg|
| |290| | | | |295| | | | |300| | | | |
|Ile|Asp|Gln|Ala|Arg|Arg|Ser|Leu|Glu|Arg|Thr|Leu|Ser|Gly|Lys|Gly|
|305| | | | |310| | | | |315| | | | |320|
|Pro|Glu|Lys|Glu|Leu|Leu|Val|Ser|Met|Glu|Leu|Asp|Lys|Ile|Lys|Thr|
| | | | |325| | | | |330| | | | |335| |
|Thr|Ile|Glu|Lys|Glu|Gln|Lys|Met|Ser|Asp|Glu|Gly|Thr|Tyr|Trp|Asp|
| | | |340| | | | |345| | | | |350| | |
|Cys|Val|Lys|Asp|Gly|Ile|Asn|Arg|Arg|Thr|Arg|Ile|Ala|Cys|Leu|
| | |355| | | | |360| | | | |365| | | |
|Cys|Trp|Ile|Gly|Gln|Cys|Ser|Cys|Gly|Ala|Ser|Leu|Ile|Gly|Tyr|Ser|
| |370| | | | |375| | | | |380| | | | |
|Thr|Tyr|Phe|Tyr|Glu|Lys|Ala|Gly|Val|Ser|Thr|Asp|Thr|Ala|Phe|Thr|
|385| | | | |390| | | | |395| | | | |400|
|Phe|Ser|Ile|Ile|Gln|Tyr|Cys|Leu|Gly|Ile|Ala|Ala|Thr|Phe|Ile|Ser|
| | | | |405| | | | |410| | | | |415| |
|Trp|Trp|Ala|Ser|Lys|Tyr|Cys|Gly|Arg|Phe|Asp|Leu|Tyr|Ala|Phe|Gly|
| | | |420| | | | |425| | | | |430| | |
|Leu|Ala|Phe|Gln|Ala|Ile|Met|Phe|Phe|Ile|Ile|Gly|Gly|Leu|Gly|Cys|
| | |435| | | | |440| | | | |445| | | |
|Ser|Asp|Thr|His|Gly|Ala|Lys|Met|Gly|Ser|Gly|Ala|Leu|Leu|Met|Val|
| |450| | | | |455| | | | |460| | | | |
|Val|Ala|Phe|Phe|Tyr|Asn|Leu|Gly|Ile|Ala|Pro|Val|Val|Phe|Cys|Leu|
|465| | | | |470| | | | |475| | | | |480|
|Val|Ser|Glu|Ile|Pro|Ser|Ser|Arg|Leu|Arg|Thr|Lys|Thr|Ile|Ile|Leu|
| | | | |485| | | | |490| | | | |495| |
|Ala|Arg|Asn|Ala|Tyr|Asn|Val|Ile|Gln|Val|Val|Val|Thr|Val|Leu|Ile|
| | | |500| | | | |505| | | | |510| | |
|Met|Tyr|Gln|Leu|Asn|Ser|Glu|Lys|Trp|Asn|Trp|Gly|Ala|Lys|Ser|Gly|
| | |515| | | | |520| | | | |525| | | |
|Phe|Phe|Trp|Gly|Gly|Phe|Cys|Leu|Ala|Thr|Leu|Ala|Trp|Ala|Val|Val|
| |530| | | | |535| | | | |540| | | | |
|Asp|Leu|Pro|Glu|Thr|Ala|Gly|Arg|Thr|Phe|Ile|Glu|Ile|Asn|Glu|Leu|
|545| | | | |550| | | | |555| | | | |560|
|Phe|Arg|Leu|Gly|Val|Pro|Ala|Arg|Lys|Phe|Lys|Ser|Thr|Lys|Val|Asp|
| | | | |565| | | | |570| | | | |575| |
|Pro|Phe|Ala|Ala|Ala|Lys|Ala|Ala|Ala|Ala|Glu|Ile|Asn|Val|Lys|Asp|
| | | |580| | | | |585| | | | |590| | |
|Pro|Lys|Glu|Asp|Leu|Glu|Thr|Ser|Val|Val|Asp|Glu|Gly|Arg|Asn|Thr|
| | |595| | | | |600| | | | |605| | | |
|Ser|Ser|Val|Val|Asn|Lys|
| |610| | | | |

<210> SEQ ID NO 5
<211> LENGTH: 1842
<212> TYPE: DNA
<213> ORGANISM: Saccharomyces cerevisiae

```
<220> FEATURE:
<221> NAME/KEY: CDS
<222> LOCATION: (1)..(1842)
<223> OTHER INFORMATION: Mal61 Transporter Protein

<400> SEQUENCE: 5 atg aag gga tta tcc tca tta ata aac aga aaa aaa gac agg aac gac      48
Met Lys Gly Leu Ser Ser Leu Ile Asn Arg Lys Lys Asp Arg Asn Asp
1               5                   10                  15 tca cac tta gat gag atc gag aat ggc gtg aac gct acc gaa ttc aac      96
Ser His Leu Asp Glu Ile Glu Asn Gly Val Asn Ala Thr Glu Phe Asn
                20                  25                  30 tcg ata gag atg gag gag caa ggt aag aaa agt gat ttt gat ctt tcc     144
Ser Ile Glu Met Glu Glu Gln Gly Lys Lys Ser Asp Phe Asp Leu Ser
            35                  40                  45 cat ctt gag tac ggt cca ggt tca cta ata cca aac gat aat aat gaa     192
His Leu Glu Tyr Gly Pro Gly Ser Leu Ile Pro Asn Asp Asn Asn Glu
        50                  55                  60 gaa gtc ccc gac ctt ctc gat gaa gct atg cag gac gcc aaa gag gca     240
Glu Val Pro Asp Leu Leu Asp Glu Ala Met Gln Asp Ala Lys Glu Ala
65                  70                  75                  80 gat gaa agt gag agg gga atg cca ctc atg aca gct ttg aag aca tat     288
Asp Glu Ser Glu Arg Gly Met Pro Leu Met Thr Ala Leu Lys Thr Tyr
                85                  90                  95 cca aaa gct gct gct tgg tca cta tta gtt tcc aca aca ttg att caa     336
Pro Lys Ala Ala Ala Trp Ser Leu Leu Val Ser Thr Thr Leu Ile Gln
            100                 105                 110 gag ggt tat gac aca gcc att cta gga gct ttc tat gcc ctg cct gtt     384
Glu Gly Tyr Asp Thr Ala Ile Leu Gly Ala Phe Tyr Ala Leu Pro Val
        115                 120                 125 ttt caa aaa aaa tat ggt tct ttg aat agc aat aca gga gat tat gaa     432
Phe Gln Lys Lys Tyr Gly Ser Leu Asn Ser Asn Thr Gly Asp Tyr Glu
    130                 135                 140 att tca gtt tcc tgg caa atc ggt cta tgt cta tgc tac atg gca ggt     480
Ile Ser Val Ser Trp Gln Ile Gly Leu Cys Leu Cys Tyr Met Ala Gly
145                 150                 155                 160 gag att gtc ggt ttg caa gtg act ggg cct tct gta gat tac atg ggc     528
Glu Ile Val Gly Leu Gln Val Thr Gly Pro Ser Val Asp Tyr Met Gly
                165                 170                 175 aac cgt tac act ctg atc atg gcg ttg ttt ttt tta gcg gct ttc att     576
Asn Arg Tyr Thr Leu Ile Met Ala Leu Phe Phe Leu Ala Ala Phe Ile
            180                 185                 190 ttc att ctg tat ttt tgc aag agt ttg ggt atg att gcc gtg gga cag     624
Phe Ile Leu Tyr Phe Cys Lys Ser Leu Gly Met Ile Ala Val Gly Gln
        195                 200                 205 gca ttg tgt ggt atg cca tgg ggt tgt ttc caa tgt ttg acc gtt tct     672
Ala Leu Cys Gly Met Pro Trp Gly Cys Phe Gln Cys Leu Thr Val Ser
    210                 215                 220 tat gct tct gaa att tgt cct ttg gcc cta aga tac tat ttg acg act     720
Tyr Ala Ser Glu Ile Cys Pro Leu Ala Leu Arg Tyr Tyr Leu Thr Thr
225                 230                 235                 240 tat tct aat tta tgt tgg acg ttc ggt caa ctt ttc gct gct ggt att     768
Tyr Ser Asn Leu Cys Trp Thr Phe Gly Gln Leu Phe Ala Ala Gly Ile
                245                 250                 255 atg aaa aat tcc cag aac aaa tat gcc aac tca gaa cta gga tat aag     816
Met Lys Asn Ser Gln Asn Lys Tyr Ala Asn Ser Glu Leu Gly Tyr Lys
            260                 265                 270 cta cct ttt gct ttg cag tgg atc tgg ccc ctt cct ttg gcg gta ggt     864
Leu Pro Phe Ala Leu Gln Trp Ile Trp Pro Leu Pro Leu Ala Val Gly
        275                 280                 285 att ttt ttg gca cca gag tct cca tgg tgg ctg gtt aaa aaa gga agg     912
```

```
                    Ile Phe Leu Ala Pro Glu Ser Pro Trp Trp Leu Val Lys Lys Gly Arg
                        290                 295                 300 att gat cag gcg agg aga tca ctt gaa aga ata tta agt ggt aaa gga        960
Ile Asp Gln Ala Arg Arg Ser Leu Glu Arg Ile Leu Ser Gly Lys Gly
305                 310                 315                 320 ccc gag aaa gaa tta cta gtg agt atg gaa ctc gat aaa atc aaa act       1008
Pro Glu Lys Glu Leu Leu Val Ser Met Glu Leu Asp Lys Ile Lys Thr
                325                 330                 335 act ata gaa aag gag cag aaa atg tct gat gaa gga act tac tgg gat       1056
Thr Ile Glu Lys Glu Gln Lys Met Ser Asp Glu Gly Thr Tyr Trp Asp
        340                 345                 350 tgt gtg aaa gat ggt att aac agg aga aga acg aga ata gct tgt tta       1104
Cys Val Lys Asp Gly Ile Asn Arg Arg Arg Thr Arg Ile Ala Cys Leu
355                 360                 365 tgt tgg atc ggt caa tgc tcc tgt ggt gca tca tta att ggt tat tca       1152
Cys Trp Ile Gly Gln Cys Ser Cys Gly Ala Ser Leu Ile Gly Tyr Ser
        370                 375                 380 act tac ttt tat gaa aaa gct ggt gtt agc act gat acg gct ttt act       1200
Thr Tyr Phe Tyr Glu Lys Ala Gly Val Ser Thr Asp Thr Ala Phe Thr
385                 390                 395                 400 ttc agt att atc caa tat tgt ctt ggt att gct gca acg ttt gta tcc       1248
Phe Ser Ile Ile Gln Tyr Cys Leu Gly Ile Ala Ala Thr Phe Val Ser
                405                 410                 415 tgg tgg gct tca aaa tat tgt ggc aga ttt gac ctt tat gct ttt ggg       1296
Trp Trp Ala Ser Lys Tyr Cys Gly Arg Phe Asp Leu Tyr Ala Phe Gly
            420                 425                 430 ctg gct ttt cag gct att atg ttc ttc att atc ggt ggt tta gga tgt       1344
Leu Ala Phe Gln Ala Ile Met Phe Phe Ile Ile Gly Gly Leu Gly Cys
        435                 440                 445 tca gac act cat ggc gct aaa atg ggt agt ggt gct ctt cta atg gtt       1392
Ser Asp Thr His Gly Ala Lys Met Gly Ser Gly Ala Leu Leu Met Val
450                 455                 460 gtc gcg ttc ttt tac aac ctc ggt att gca cct gtt gtt ttt tgc tta       1440
Val Ala Phe Phe Tyr Asn Leu Gly Ile Ala Pro Val Val Phe Cys Leu
465                 470                 475                 480 gtg tct gaa atg ccg tct tca agg cta aga acc aaa aca att att ttg       1488
Val Ser Glu Met Pro Ser Ser Arg Leu Arg Thr Lys Thr Ile Ile Leu
                485                 490                 495 gct cgt aat gct tac aat gtg atc caa gtt gta gtt aca gtt tgg atc       1536
Ala Arg Asn Ala Tyr Asn Val Ile Gln Val Val Val Thr Val Leu Ile
            500                 505                 510 atg tac caa ttg aac tca gag aaa tgg aat tgg ggt gct aaa tca ggc       1584
Met Tyr Gln Leu Asn Ser Glu Lys Trp Asn Trp Gly Ala Lys Ser Gly
        515                 520                 525 ttt ttc tgg gga gga ttt tgt ctg gcc act tta gct tgg gct gtt gtc       1632
Phe Phe Trp Gly Gly Phe Cys Leu Ala Thr Leu Ala Trp Ala Val Val
530                 535                 540 gat tta cca gaa acc gct ggc agg act ttt att gag ata aat gaa ttg       1680
Asp Leu Pro Glu Thr Ala Gly Arg Thr Phe Ile Glu Ile Asn Glu Leu
545                 550                 555                 560 ttt aga ctt ggt gtt cca gca aga aag ttc aag tcg act aaa gtc gac       1728
Phe Arg Leu Gly Val Pro Ala Arg Lys Phe Lys Ser Thr Lys Val Asp
                565                 570                 575 cct ttt gca gct gcc aaa gca gca gct gca gaa att aat gtt aaa gat       1776
Pro Phe Ala Ala Ala Lys Ala Ala Ala Ala Glu Ile Asn Val Lys Asp
            580                 585                 590 ccg aag gaa gat ttg gaa act tct gtg gta gat gaa ggg cga agc acc       1824
Pro Lys Glu Asp Leu Glu Thr Ser Val Val Asp Glu Gly Arg Ser Thr
        595                 600                 605 cca tct gtt gtg aac aaa                                               1842
```

Pro Ser Val Val Asn Lys
    610

<210> SEQ ID NO 6
<211> LENGTH: 614
<212> TYPE: PRT
<213> ORGANISM: Saccharomyces cerevisiae

<400> SEQUENCE: 6

Met Lys Gly Leu Ser Ser Leu Ile Asn Arg Lys Lys Asp Arg Asn Asp
1               5                   10                  15

Ser His Leu Asp Glu Ile Glu Asn Gly Val Asn Ala Thr Glu Phe Asn
            20                  25                  30

Ser Ile Glu Met Glu Glu Gln Gly Lys Lys Ser Asp Phe Asp Leu Ser
        35                  40                  45

His Leu Glu Tyr Gly Pro Gly Ser Leu Ile Pro Asn Asp Asn Asn Glu
    50                  55                  60

Glu Val Pro Asp Leu Leu Asp Glu Ala Met Gln Asp Ala Lys Glu Ala
65                  70                  75                  80

Asp Glu Ser Glu Arg Gly Met Pro Leu Met Thr Ala Leu Lys Thr Tyr
                85                  90                  95

Pro Lys Ala Ala Ala Trp Ser Leu Leu Val Ser Thr Thr Leu Ile Gln
            100                 105                 110

Glu Gly Tyr Asp Thr Ala Ile Leu Gly Ala Phe Tyr Ala Leu Pro Val
        115                 120                 125

Phe Gln Lys Lys Tyr Gly Ser Leu Asn Ser Asn Thr Gly Asp Tyr Glu
    130                 135                 140

Ile Ser Val Ser Trp Gln Ile Gly Leu Cys Leu Cys Tyr Met Ala Gly
145                 150                 155                 160

Glu Ile Val Gly Leu Gln Val Thr Gly Pro Ser Val Asp Tyr Met Gly
                165                 170                 175

Asn Arg Tyr Thr Leu Ile Met Ala Leu Phe Phe Leu Ala Ala Phe Ile
            180                 185                 190

Phe Ile Leu Tyr Phe Cys Lys Ser Leu Gly Met Ile Ala Val Gly Gln
        195                 200                 205

Ala Leu Cys Gly Met Pro Trp Gly Cys Phe Gln Cys Leu Thr Val Ser
    210                 215                 220

Tyr Ala Ser Glu Ile Cys Pro Leu Ala Leu Arg Tyr Tyr Leu Thr Thr
225                 230                 235                 240

Tyr Ser Asn Leu Cys Trp Thr Phe Gly Gln Leu Phe Ala Ala Gly Ile
                245                 250                 255

Met Lys Asn Ser Gln Asn Lys Tyr Ala Asn Ser Glu Leu Gly Tyr Lys
            260                 265                 270

Leu Pro Phe Ala Leu Gln Trp Ile Trp Pro Leu Pro Leu Ala Val Gly
        275                 280                 285

Ile Phe Leu Ala Pro Glu Ser Pro Trp Trp Leu Val Lys Lys Gly Arg
    290                 295                 300

Ile Asp Gln Ala Arg Arg Ser Leu Glu Arg Ile Leu Ser Gly Lys Gly
305                 310                 315                 320

Pro Glu Lys Glu Leu Leu Val Ser Met Glu Leu Asp Lys Ile Lys Thr
                325                 330                 335

Thr Ile Glu Lys Glu Gln Lys Met Ser Asp Glu Gly Thr Tyr Trp Asp
            340                 345                 350

Cys Val Lys Asp Gly Ile Asn Arg Arg Arg Thr Arg Ile Ala Cys Leu
        355                 360                 365

```
Cys Trp Ile Gly Gln Cys Ser Cys Gly Ala Ser Leu Ile Gly Tyr Ser
            370                 375                 380

Thr Tyr Phe Tyr Glu Lys Ala Gly Val Ser Thr Asp Thr Ala Phe Thr
385                 390                 395                 400

Phe Ser Ile Ile Gln Tyr Cys Leu Gly Ile Ala Ala Thr Phe Val Ser
                405                 410                 415

Trp Trp Ala Ser Lys Tyr Cys Gly Arg Phe Asp Leu Tyr Ala Phe Gly
            420                 425                 430

Leu Ala Phe Gln Ala Ile Met Phe Ile Ile Gly Leu Gly Cys
        435                 440                 445

Ser Asp Thr His Gly Ala Lys Met Gly Ser Gly Ala Leu Leu Met Val
450                 455                 460

Val Ala Phe Phe Tyr Asn Leu Gly Ile Ala Pro Val Val Phe Cys Leu
465                 470                 475                 480

Val Ser Glu Met Pro Ser Ser Arg Leu Arg Thr Lys Thr Ile Leu
                485                 490                 495

Ala Arg Asn Ala Tyr Asn Val Ile Gln Val Val Thr Val Leu Ile
            500                 505                 510

Met Tyr Gln Leu Asn Ser Glu Lys Trp Asn Trp Gly Ala Lys Ser Gly
        515                 520                 525

Phe Phe Trp Gly Gly Phe Cys Leu Ala Thr Leu Ala Trp Ala Val Val
530                 535                 540

Asp Leu Pro Glu Thr Ala Gly Arg Thr Phe Ile Glu Ile Asn Glu Leu
545                 550                 555                 560

Phe Arg Leu Gly Val Pro Ala Arg Lys Phe Lys Ser Thr Lys Val Asp
                565                 570                 575

Pro Phe Ala Ala Ala Lys Ala Ala Ala Glu Ile Asn Val Lys Asp
            580                 585                 590

Pro Lys Glu Asp Leu Glu Thr Ser Val Val Asp Glu Gly Arg Ser Thr
        595                 600                 605

Pro Ser Val Val Asn Lys
    610

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agagctcagc atataaagag aca                                             23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggatccgta tctacctact gg                                              22

<210> SEQ ID NO 9
<211> LENGTH: 1845
<212> TYPE: DNA
<213> ORGANISM: Saccharomyces cerevisiae
```

<400> SEQUENCE: 9

```
atgaaggat tatcctcatt aataaacaga aaaaagaca ggaacgactc acacttagat      60
gagatcgaga atggcgtgaa cgctaccgaa ttcaactcga tagagatgga ggagcaaggt     120
aagaaaagtg attttggtct ttcccatcat gagtacggtc caggttcact aataccaaac    180
gataataatg aagaagtccc cgaccttctc gatgaagcta tgcaggacgc caagaggca     240
gatgaaagtg agagggaat gccactcatg acagctttga agacatatcc aaaagctgct    300
gcttggtcac tattagtttc cacaacattg attcaagagg ttatgacac agccattcta     360
ggagctttct atgccctgcc tgttttcaa aaaaaatatg gttctttgaa tagcaataca    420
ggagattatg aaattcagt ttcttggcaa atcggtctat gtctatgcta catggcaggt     480
gaaattgtgg ggctacagct aacgggggccc tccgtggatc ttgttggaaa tcgttacaca   540
ttgatcatgg cgttgttctt tttagcggct tcatttttca ttctgtattt ttgcaagagt   600
ttgggtatga ttgccgtggg acaggcattg tgtggtatgc catggggttg tttccaatgt   660
ttgaccgttt cttatgcttc tgaaatttgt cctttggccc taagatacta tttgacgact   720
tattctaatt tatgttggac gttcggtcaa cttttcgctg ctggtattat gaaaaattcc    780
cagaacaaat atgccaactc agaactagga tataagctac cttttgcttt gcagtggatc    840
tggcccttc ctttggcggt aggtattttt tttgcaccag agtctccatg gtggctggtt    900
aaaaaaggaa ggattgatca agcgaggaga tcacttgaaa gaacattaag tggtaaagga    960
cccgagaaag aattactagt gactatggaa ctcgataaaa tcaaaactac tatagaaaag   1020
gagcagaaaa tgtctgatga aggaacttac tgggattgtg tgaaagatgg tattaacagg   1080
agaagaacga gaatagcttg tttatgttgg atcggtcaat gctcctgtgg tgcatcatta   1140
attggttatt caacttactt ttatgaaaaa gctggtgtta gcactgatac ggcttttact   1200
ttcagtatta tccaatattg tcttggtatt gctgcaacgt tgtatcctg gtgggcttca    1260
aaatattgtg gcagatttga cctttatgct tttgggctgg ctttttcaggc tattatgttc   1320
ttcattatcg gtggtttagg atgttcagac actcatggcg ctaaaatggg tagtggtgct   1380
cttctaatgg ttgtcgcgtt cttttacaac ctcggtattg cacctgttgt ttttgctta    1440
gtgtctgaaa tgccgtcttc aaggctaaga accaaaacaa ttattttggc tcgtaatgct   1500
tacaatgtga tccaagttgt agttacagtt ttgattatgt accaattgaa ctcagagaaa    1560
tggaattggg gtgctaaatc aggcttttc tggggaggat tttgtctggc cactttagct    1620
tgggctgttg tcgatttacc agaaaccgct ggcaggactt ttattgagat aaatgaattg    1680
tttagacttg gtgttccagc aagaaagttc aagtcgacta agtcgaccc ttttgcagct    1740
gccaaagcag cagctgcaga aattaatgtt aaagatccga aggaagattt ggaaacttct   1800
gtggtagatg aagggcgaaa cacctcatct gttgtgaaca aatga                    1845
```

<210> SEQ ID NO 10
<211> LENGTH: 1845
<212> TYPE: DNA
<213> ORGANISM: Saccharomyces cerevisiae

<400> SEQUENCE: 10

```
atgaaggat tatcctcatt aataaacaga aaaaagaca ggaacgactc acacttagat      60
gagatcgaga atggcgtgaa cgctaccgaa ttcaactcga tagagatgga ggagcaaggt     120
aagaaaagtg attttgatct ttcccatctt gagtacggtc caggttcact aataccaaac    180
gataataatg aagaagtccc cgaccttctc gatgaagcta tgcaggacgc caagaggca     240
```

```
gatgaaagtg agagggaat gccactcatg acagctttga agacatatcc aaaagctgct    300
gcttggtcac tattagtttc cacaacattg attcaagagg ttatgacac agccattcta    360
ggagctttct atgccctgcc tgtttttcaa aaaaaatatg gttctttgaa tagcaataca   420
ggagattatg aaatttcagt ttcctggcaa atcggtctat gtctatgcta catggcaggt   480
gagattgtcg gtttgcaaat gactgggcct tctgtagatt acatgggcaa ccgttacact   540
ctgatcatgg cgttgttctt tttagcggct ttcattttca ttctgtattt ttgcaagagt   600
ttgggtatga ttgccgtggg acaggcattg tgtggtatgc catggggttg tttccaatgt   660
ttgaccgttt cttatgcttc tgaaatttgt cctttggccc taagatacta tttgacgact   720
tattctaatt tatgttgggc gttcggtcaa cttttcgctg ctggtattat gaaaaattcc   780
cagaacaaat atgccaactc agaactagga tataagctac cttttgcttt gcagtggatc   840
tggccccttc cttggcggt aggtatttt tttgcaccag agtctccatg gtggctggtt    900
aaaaaaggaa ggattgatca agcgaggaga tcacttgaaa gaacattaag tggtaaagga   960
cccgagaaag aattactagt gagtatggaa ctcgataaaa tcaaaactac tatagaaaag  1020
gagcagaaaa tgtctgatga aggaacttac tgggattgtg tgaaagatgg tattaacagg  1080
agaagaacga gaatagcttg tttatgttgg atcggtcaat gctcctgtgg tgcatcatta  1140
attggttatt caacttactt ttatgaaaaa gctggtgtta gcactgatac ggcttttact  1200
ttcagtatta tccaatattg tcttggtatt gctgcaacgt ttatatcctg gtgggcttca  1260
aaatattgtg gcagatttga cctttatgct ttttgggctgg cttttcaggc tattatgttc  1320
ttcattatcg gtggtttagg atgttcagac actcatggcg ctaaaatggg tagtggtgct  1380
cttctaatgg ttgtcgcgtt cttttacaac ctcggtattg cacctgttgt tttttgctta  1440
gtgtctgaaa taccgtcttc aaggctaaga accaaaacaa ttatttggc tcgtaatgct   1500
tacaatgtga tccaagttgt agttacagtt ttgatcatgt accaattgaa ctcagagaaa   1560
tggaattggg gtgctaaatc aggcttttc tggggaggat tttgtctggc cactttagct   1620
tgggctgttg tcgatttacc agaaaccgct ggcaggactt ttattgagat aaatgaattg   1680
tttagacttg gtgttccagc aagaaagttc aagtcgacta aagtcgaccc ttttgcagct   1740
gccaaagcag cagctgcaga aattaatgtt aaagatccga aggaagattt ggaaacttct   1800
gtggtagatg aagggcgaaa cacctcatct gttgtgaaca aatga                  1845
```

<210> SEQ ID NO 11
<211> LENGTH: 1845
<212> TYPE: DNA
<213> ORGANISM: Saccharomyces cerevisiae

<400> SEQUENCE: 11

```
atgaaggat tatcctcatt aataaacaga aaaaagaca ggaacgactc acacttagat     60
gagatcgaga atggcgtgaa cgctaccgaa ttcaactcga tagagatgga ggagcaaggt  120
aagaaaagtg attttgatct tccccatctt gagtacggtc caggttcact aataccaaac  180
gataataatg aagaagtccc cgaccttctc gatgaagcta tgcaggacgc caaagaggca  240
gatgaaagtg agagggaat gccactcatg acagctttga agacatatcc aaaagctgct   300
gcttggtcac tattagtttc cacaacattg attcaagagg ttatgacac agccattcta  360
ggagctttct atgccctgcc tgtttttcaa aaaaaatatg gttctttgaa tagcaataca  420
ggagattatg aaatttcagt ttcctggcaa atcggtctat gtctatgcta catggcaggt  480
gagattgtcg gtttgcaagt gactgggcct tctgtagatt acatgggcaa ccgttacact  540
```

```
-continued ctgatcatgg cgttgttctt tttagcggct ttcattttca ttctgtatttt ttgcaagagt    600 ttgggtatga ttgccgtggg acaggcattg tgtggtatgc catggggttg tttccaatgt    660
ttgaccgttt cttatgcttc tgaaatttgt cctttggccc taagatacta tttgacgact    720
tattctaatt tatgttggac gttcggtcaa cttttcgctg ctggtattat gaaaaattcc    780
cagaacaaat atgccaactc agaactagga tataagctac cttttgcttt gcagtggatc    840 tggcccttc ctttggcggt aggtattttt ttggcaccag agtctccatg gtggctggtt    900
aaaaaaggaa ggattgatca ggcgaggaga tcacttgaaa gaatattaag tggtaaagga    960
cccgagaaag aattactagt gagtatgaa ctcgataaaa tcaaaactac tatagaaaag   1020
gagcagaaaa tgtctgatga aggaacttac tgggattgtg tgaaagatgg tattaacagg   1080
agaagaacga gaatagcttg tttatgttgg atcggtcaat gctcctgtgg tgcatcatta   1140
attggttatt caacttactt ttatgaaaaa gctggtgtta gcactgatac ggcttttact   1200
ttcagtatta tccaatattg tcttggtatt gctgcaacgt ttgtatcctg gtgggcttca   1260
aaatattgtg gcagatttga cctttatgct tttgggctgg cttttcaggc tattatgttc   1320
ttcattatcg gtggtttagg atgttcagac actcatggcg ctaaaatggg tagtggtgct   1380
cttctaatgg ttgtcgcgtt cttttacaac ctcggtattg cacctgttgt tttttgctta   1440
gtgtctgaaa tgccgtcttc aaggctaaga accaaaacaa ttattttggc tcgtaatgct   1500
tacaatgtga tccaagttgt agttacagtt ttgatcatgt accaattgaa ctcagagaaa   1560
tggaattggg gtgctaaatc aggcttttc tggggaggat tttgtctggc cactttagct   1620
tgggctgttg tcgatttacc agaaaccgct ggcaggactt ttattgagat aaatgaattg   1680
tttagacttg gtgttccagc aagaaagttc aagtcgacta aagtcgaccc ttttgcagct   1740
gccaaagcag cagctgcaga aattaatgtt aaagatccga aggaagattt ggaaacttct   1800
gtggtagatg aagggcgaag caccccatct gttgtgaaca aatga                  1845
```

GLUCOSE-INDUCED INACTIVATION/DEGRADATION-RESISTANT TRANSPORTER GENE AND USE THEREOF

TECHNICAL FIELD

The present invention relates to a glucose-induced inactivation/degradation transporter gene and use thereof, and more particularly to a brewing yeast having an excellent assimilability of oligosaccharides (maltose, maltotriose, etc.), an alcoholic beverage prepared using the yeast, a method of producing the alcoholic beverage, and so on.

BACKGROUND ART

In the production of malt fermented beverages such as beer, happoshu (low-malt beer), whisky, etc., the major three sugars contained in a wort prepared by mashing a malt, etc. are glucose, maltose and maltotriose. The ratio of these malt-derived sugars can be somewhat varied depending on the mashing process and may be approximately 1:5:1, since the ratio does not change significantly when enzyme preparations, glycosylated starch, etc. are not added. Among them, glucose is a monosaccharide and preferentially assimilated as a sugar most favored by yeast.

Yeast has numerous genes suppressed in the presence of glucose during the transcription process. This regulatory suppression is called glucose repression. Several transporters required for the uptake of maltose or maltotriose into yeast all undergo this repression. It is known that some of these gene products which undergo glucose repression are inactivated in the presence of glucose even after translation. α-Glucoside transporters are also within this type and known to be rapidly degraded in the presence of glucose. The first step of assimilation of maltose or maltotriose is its uptake into yeast cells by these transporters and when transporters are degraded, assimilation of these sugars is discontinued. This is the reason why the expression of transporter is called a rate-determining step for assimilation.

Non-Patent Document 1: Brondijk, T. H., van der Rest, M. E., Pluim, D., de Vries, Y. de., Stingl, K., Poolman, B. and Konings, W. N. (1998) J. Biol. Chem., 273 (25), 15352-15357

Non-Patent Document 2: Medintz, I., Wang, X., Hradek, T. and Michels, C. A. (2000) Biochemistry, 39 (15), 4518-4526

Non-Patent Document 3: Gadura, N. and Michels, C. A. (2006) Curr. Genet., 50 (2), 101-114

DISCLOSURE OF INVENTION

Under such situations, it has been desired to provide a yeast bearing an oligosaccharide transporter less susceptible to glucose-induced inactivation or degradation and having an improved assimilation of oligosaccharides such as maltose, etc.

The present inventors have made extensive efforts to solve the foregoing problems. As a result, the inventors have developed a novel method of screening a transporter, which is less susceptible to glucose-induced inactivation or degradation (hereinafter referred to as "glucose-induced inactivation/degradation-resistant transporter") or a yeast expressing the transporter and based on the screening method, found the glucose-induced inactivation/degradation-resistant transporter or a yeast bearing the same. The present invention has thus been accomplished.

In other words, the present invention relates to a gene encoding the glucose-induced inactivation/degradation-resistant transporter, a transporter protein encoded by the gene, a transformed yeast in which expression of the gene is regulated, a method of producing an alcoholic beverage which comprises using the yeast in which expression of the gene is regulated, etc. More specifically, the present invention provides the polynucleotides given below, vectors comprising the polynucleotides, transformed yeasts in which the vectors are introduced, and a method of producing alcoholic beverages using these transformed yeasts.

(1) A polynucleotide selected from the group consisting of (a) to (f) below:
(a) a polynucleotide comprising a polynucleotide consisting of the nucleotide sequence of SEQ ID NO: 1;
(b) a polynucleotide comprising a polynucleotide encoding a protein consisting of the amino acid sequence of SEQ ID NO: 2;
(c) a polynucleotide comprising a polynucleotide consisting of an amino acid sequence wherein 1 to 15 amino acids are deleted, substituted, inserted and/or added in the amino acid sequence of SEQ ID NO: 2, and encoding a transporter protein having a resistance to glucose-induced inactivation/degradation;
(d) a polynucleotide comprising a polynucleotide comprising an amino acid sequence having an identity of at least 90% with the amino acid sequence of SEQ ID NO: 2, and encoding a transporter protein having a resistance to glucose-induced inactivation/degradation;
(e) a polynucleotide comprising a polynucleotide hybridizing with a polynucleotide consisting of a nucleotide sequence complementary to the nucleotide sequence of SEQ ID NO: 1 under stringent conditions, and encoding a transporter protein having a resistance to glucose-induced inactivation/degradation; and,
(f) a polynucleotide comprising a polynucleotide hybridizing with a polynucleotide consisting of a nucleotide sequence complementary to the nucleotide sequence of a polynucleotide encoding a protein consisting of the amino acid sequence of SEQ ID NO: 2 under stringent conditions, and encoding a transporter protein having a resistance to glucose-induced inactivation/degradation.

(2) The polynucleotide according to (1), which is selected from the group consisting of (g) to (i) below:
(g) a polynucleotide comprising a polynucleotide encoding a transporter protein consisting of the amino acid sequence of SEQ ID NO: 2, or the amino acid sequence of SEQ ID NO: 2 wherein 1 to 5 amino acids are deleted, substituted, inserted and/or added in the amino acid sequence, and having a resistance to glucose-induced inactivation/degradation;
(h) a polynucleotide comprising a polynucleotide encoding a transporter protein comprising the amino acid sequence having an identity of at least 97% with the amino acid sequence of SEQ ID NO: 2, and having a resistance to glucose-induced inactivation/degradation; and,
(i) a polynucleotide comprising a polynucleotide hybridizing with a polynucleotide consisting of the nucleotide sequence of SEQ ID NO: 1 or with a polynucleotide consisting of a nucleotide sequence complementary to the nucleotide sequence of SEQ ID NO: 1 under high stringent conditions, and encoding a transporter protein having a resistance to glucose-induced inactivation/degradation.

(3) The polynucleotide according to (1) or (2), comprising a polynucleotide consisting of the nucleotide sequence of SEQ ID NO: 1.

(4) The polynucleotide according to (1) or (2), comprising a polynucleotide encoding a protein consisting of the amino acid sequence of SEQ ID NO: 2.

(5) The polynucleotide according to any one of (1) to (4), which is a DNA.

(6) A protein encoded by the polynucleotide according to any one of (1) to (5).

(7) A vector comprising the polynucleotide according to any one of (1) to (5).

(8) A transformed yeast introduced with the vector according to (7).

(9) The yeast for brewing according to (8), wherein oligosaccharide assimilability is improved by introducing the vector according to (7).

(10) The yeast for brewing according to (8), wherein oligosaccharide assimilability is improved by increasing the expression level of the protein according to (6).

(11) A method of producing an alcoholic beverage which comprises using the yeast according to any one of (8) to (10).

(12) The method of producing an alcoholic beverage according to (11), wherein the alcoholic beverage brewed is a malt beverage.

(13) The method of producing an alcoholic beverage according to (12), wherein the alcoholic beverage brewed is wine.

(14) An alcoholic beverage produced by the method according to any one of (11) to (13).

The use of the yeast in accordance with the present invention provides the advantage that the fermentation rate of moromi mash containing oligosaccharides such as maltose, etc. can be increased. The transporter gene in accordance with the present invention can be introduced into any of brewing yeasts or laboratory yeasts. It is effective especially in the case where oligosaccharides (maltose, maltotriose, turanose, trehalose, etc.) which can be taken up by the transporter in accordance with the present invention are contained in a crude fermentation liquor abundant in monosaccharides such as glucose, fructose, etc.

BRIEF DESCRIPTION OF DRAWINGS

FIG. 2 shows the nucleotide sequence of MAL21 gene.

FIG. 3 shows the amino acid sequence of Mal21p gene.

FIG. 4-1 shows the alignment of the amino acid sequence of Mal21p/Mal31p/Mal61p.

FIG. 4-2 shows the alignment of the nucleotide sequence of Mal21p/Mal31p/Mal61p.

FIG. 4-3 is continued from FIG. 4-2.

FIG. 4-4 is continued from FIG. 4-3.

BEST MODES FOR CARRYING OUT THE INVENTION

Figure 1:
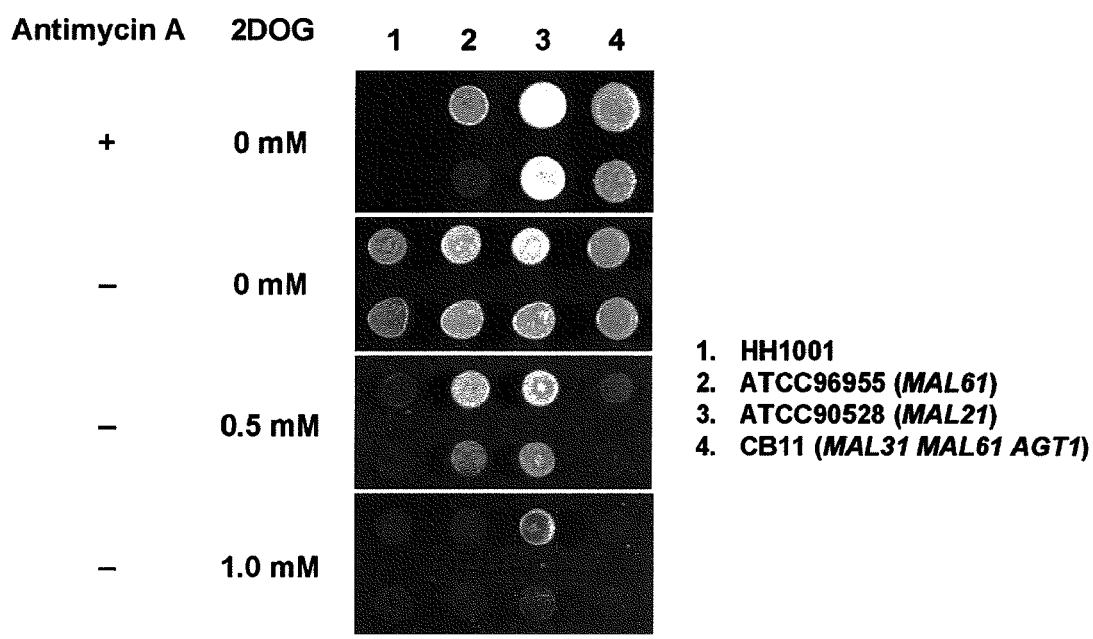
FIG. 1 shows the differences in growth between laboratory yeasts in the presence of 2-deoxyglucose.

Based on the idea that if glucose-induced inactivation or degradation of a post-translational transporter can be regulated, maltose and maltotriose can be more efficiently assimilated by a yeast in the presence of glucose, the present inventors have made extensive efforts and as a result, found Mal21p from the natural world, which is an α-glucoside transporter less susceptible to degradation, and confirmed that the degradation rate of Mal21p is extremely slow when compared to other transporters.

It has also been succeeded that by highly expressing the newly obtained transporter less susceptible to glucose-induced inactivation or degradation, the growth rate could be increased actually in a maltose medium. In addition, the assimilation rate of maltose could be increased in beer brewing. The present invention has been accomplished based on this idea and the results of studies.

In the present invention, SEQ ID NOS: 1 to 6 represent the nucleotide sequences of the following genes or the amino acid sequences of the following transporters.
[SEQ ID NO: 1] Nucleotide sequence of MAL21
[SEQ ID NO: 2] Amino acid sequence of Mal21p α-glucoside transporter
[SEQ ID NO: 3] Nucleotide sequence of MAL31
[SEQ ID NO: 4] Amino acid sequence of Mal31p α-glucoside transporter
[SEQ ID NO: 5] Nucleotide sequence of MAL61
[SEQ ID NO: 6] Amino acid sequence of Mal61p α-glucoside transporter As used herein, the term "α-glucoside transporter" refers to a protein associated with α-glucoside transport and such α-glucoside transporters include a maltose transporter, a maltotriose transporter, etc.

1. Polynucleotide of the Invention

First, the present invention provides (a) a polynucleotide comprising the polynucleotide consisting of the nucleotide sequence of SEQ ID NO: 1; and (2) a polynucleotide comprising the polynucleotide encoding a protein consisting of the amino acid sequence of SEQ ID NO: 2. The polynucleotide may be DNA or RNA.

The polynucleotide intended in the present invention is not limited to polynucleotides encoding the proteins having the sequences described above but includes other polynucleotides encoding proteins functionally equivalent to the proteins having the above sequences. The functionally equivalent proteins include, for example, (c) a transporter protein comprising an amino acid sequence in which 1 to 15 (preferably 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2 or 1) amino acids are deleted, substituted, inserted and/or added in the amino acid sequence of SEQ ID NO: 2, and having the resistance to glucose-induced inactivation/degradation.

Such proteins include a transporter protein comprising an amino acid sequence in which, for example, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2 or 1 amino acid residue is deleted, substituted, inserted and/or added in the amino acid sequence of SEQ ID NO: 2, and having the resistance to glucose-induced inactivation/degradation. In general, the smaller number of the deletion, substitution, insertion and/or addition of the amino acid residues above is preferred. Such proteins include (d) transporter proteins comprising an amino acid sequence having the identity of at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8% and at least about 99.9%, with the amino acid sequence of SEQ ID NO: 2, and having the resistance to glucose-induced inactivation/degradation. In general, the larger numerical value of the homology described above is more preferred.

<Assessment of Resistance to Glucose-Induced Inactivation/Degradation>

According to the present invention, the resistance to glucose-induced inactivation/degradation can be evaluated, for example, by the following procedures. First, it is confirmed that a strain expressing each transporter protein is able to grow in a 2% maltose-supplemented synthetic complete medium (SCM) containing 0 to 2.0 mM of 2-deoxyglucose (6.7 g/L of yeast nitrogen base w/o amino acids, 20 g/L of maltose, 20 mg/ml of adenine sulfate, 20 mg/ml of uracil, 20 mg/ml of L-tryptophan, 20 mg/ml of L-histidine hydrochloride, 20 mg/ml of L-arginine hydrochloride, 20 mg/ml of L-methionine, 30 mg/ml of L-tyrosine, 30 mg/ml of L-leucine, 30 mg/ml of L-isoleucine, 30 mg/ml of L-lysine hydrochloride, 50 mg/ml of L-phenylalanine, 100 mg/ml of L-glutamic acid, 100 mg/ml of L-aspartic acid, 150 mg/ml of L-valine, 200 mg/ml of L-threonine and 400 mg/ml of L-serine), or in a maltose, etc. minimum medium containing 0 to 2 mM of 2-deoxyglucose (6.7 g/L of yeast nitrogen base w/o amino acids, 20 g/L of maltose, etc.; if the transformant is auxotrophic, also containing the nutrients), to select the strain in which the transporter retains the maltose uptake activity in yeasts even where the signal of glucose-induced inactivation/degradation generates. Next, this strain is inoculated into YPD (10 g/L of yeast extract, 20 g/L of polypeptone and 20 g/L of glucose) followed by shaking the culture at 30° C. overnight. The culture broth is inoculated into a YPM medium (10 g/L of yeast extract, 20 g/L of polypeptone and 5 g/L of maltose) followed by shake culture at 30° C. for 2.5 hours to reach OD660=1.0. The cells are then collected. The 60 OD660 units of cells are measured and suspended in 30 ml of a medium for degradation rate measurement (1.7 g/L of yeast nitrogen base w/o amino acids and ammonia, 20 g/L of glucose and 25 µg/L of cycloheximide) preincubated at 30° C., followed by incubation at 30° C. The cell suspension is sampled by 5 ml at an appropriate time (0, 10, 20, 30 and 40 minutes or 0, 30, 60, 90 and 120 minutes). After the suspension is centrifuged immediately thereafter, the supernatant is discarded and the cells are frozen using an ethanol-dry ice. The transporter protein is isolated from the frozen cells in a conventional manner and the intensity of the protein band is measured to determine the half life from its diminution rate. The transporter protein preferably used in the present invention has the half life of 2 times or more, 3 times or more, 4 times or more, 5 times or more, 6 times or more or 8 times or more, than that of, e.g., Mal31p or Mal61p.

The present invention further provides (e) a polynucleotide comprising a polynucleotide hybridizing with a polynucleotide consisting of a nucleotide sequence complementary to the nucleotide sequence of SEQ ID NO: 1 under stringent conditions, and encoding a transporter protein having a resistance to glucose-induced inactivation/degradation; and, (f) a polynucleotide comprising a polynucleotide hybridizing with a polynucleotide consisting of a nucleotide sequence complementary to the nucleotide sequence of a polynucleotide encoding the protein consisting of the amino acid sequence of SEQ ID NO: 2 under stringent conditions, and encoding a transporter protein having a resistance to glucose-induced inactivation/degradation.

The polynucleotide which is preferred in the present invention includes the polynucleotides defined in (a) through (f) above, the polynucleotide comprising a polynucleotide encoding a protein consisting of the amino acid sequence of SEQ ID NO: 2, and the polynucleotide comprising a polynucleotide consisting of the nucleotide sequence of SEQ ID NO: 1, more preferably the polynucleotide defined by SEQ ID NO: 1.

As used herein, the term "polynucleotide hybridizing under stringent conditions" refers to a polynucleotide (such as DNA) obtained by the colony hybridization technique, the plaque hybridization technique, the Southern hybridization technique or the like, using as a probe all or a portion of a polynucleotide consisting of a nucleotide sequence complementary to the nucleotide sequence of SEQ ID NO: 1 or a polynucleotide encoding the amino acid sequence of SEQ ID NO: 2. For the hybridization, there may be used methods described in, for example, Molecular Cloning, 3rd Ed., Current Protocols in Molecular Biology, John Wiley & Sons, 1987-1997, etc.

As used herein, the term "stringent conditions" may be any of low stringent conditions, medium stringent conditions and high stringent conditions. The term "low stringent conditions" refers to conditions of, e.g., 5×SSC, 5×Denhardt's solution, 0.5% SDS, 50% formamide and 32° C. The term "medium stringent conditions" refers to conditions of, e.g., 5×SSC, 5×Denhardt's solution, 0.5% SDS, 50% formamide and 42° C. The term "high stringent conditions" refers to conditions of, e.g., 5×SSC, 5×Denhardt's solution, 0.5% SDS, 50% formamide and 50° C. It can be expected under these conditions that DNAs having a higher homology are efficiently obtained as the temperature becomes higher. However, there are several factors that might affect the stringency of hybridization to be considered and such factors include temperature, probe concentration, probe length, ionic strength, time, salt concentration, etc. Those skilled in the art can suitably choose these factors to achieve the same stringencies.

In the case of using commercially available kits for the hybridization, for example, Alkphos Direct Labeling Reagents (manufactured by Amersham Pharmacia) can be used. In this case, the hybridized DNA can be detected by incubating with a labeled probe overnight and washing the membrane with a primary wash buffer containing 0.1% (w/v) SDS at 55° C., according to the protocol attached to the kit.

Other DNAs that can be hybridized include DNAs having the identity of at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, or at least about 99.9%, with the DNA encoding the amino acid sequence of SEQ ID NO: 2 or 4, as calculated by a homology search software such as FASTA, BLAST, etc. using default parameters.

The identity of amino acid sequences or nucleotide sequences can be determined using the algorithm BLAST by Karlin and Altschul (Proc. Natl. Acad. Sci. USA, 87: 2264-2268, 1990; Proc. Natl. Acad. Sci. USA, 90: 5873, 1993). Based on the algorithm BLAST, programs called BLASTN and BLASTX have been developed (Altschul S. F., et al., J. Mol. Biol. 215: 403, 1990). When a nucleotide sequence is analyzed using BLASTN, the parameters are set to, for example, score=100 and word length=12. When an amino acid sequence is analyzed using BLASTX, the parameters are set to, for example, score=50 and word length=3. When BLAST and Gapped BLAST programs are used, default parameters for each of the programs are employed.

2. Protein of the Invention

The present invention also provides the protein encoded by any one of the polynucleotides (a) through (i) described above. Preferred examples of the proteins of the present invention are transporter proteins consisting of the amino acid sequence of SEQ ID NO: 2, in which 1 to 15 amino acids (preferably, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1) are deleted, substituted, inserted and/or added in the amino acid sequence, and having the resistance to glucose-induced inactivation/degradation.

Such proteins include transporter proteins consisting of the amino acid sequence of SEQ ID NO: 2, in which the aforesaid numbers of amino acid residues are deleted, substituted, inserted and/or added in the amino acid sequence, and having the resistance to glucose-induced inactivation/degradation. Such transporter proteins include transporter proteins having the amino acid sequence which has the homology described above to the amino acid sequence of SEQ ID NO: 2, and having the resistance to glucose-induced inactivation/degradation. These proteins can be obtained by site-directed mutagenesis described in Molecular Cloning, 3rd ed., Current Protocols in Molecular Biology, Nuc. Acids. Res., 10, 6487 (1982), Proc. Natl. Acad. Sci. USA, 79, 6409 (1982), Gene, 34, 315 (1985), Nuc. Acids. Res., 13, 4431 (1985), Proc. Natl. Acad. Sci. USA, 82, 488 (1985), etc.

What is meant by 1 to 15 amino acids (preferably, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1) being deleted, substituted, inserted and/or added in the amino acid sequence of proteins in accordance with the polynucleotide of the present invention refers to that the deletion, substitution, insertion and/or addition of 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1 amino acid residue(s) take place at optional positions in 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, or 1 amino acid sequence in the same sequence. Among the deletion, substitution, insertion and/or addition, two or more events may take place concurrently.

Examples of the amino acid residues which are mutually substitutable are given below. The amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention can also be produced by chemical synthesis methods such as the Fmoc method (fluorenylmethyloxycarbonyl method), the tBoc method (t-butyloxycarbonyl method) or the like. In addition, peptide synthesizers available from, for example, Advanced ChemTech, Perkin-Elmer, Pharmacia, Protein Technology Instrument, Synthecell-Vega, PerSeptive, Shimadzu Corp. can also be used for the chemical synthesis.

3. Vector of the Invention and Yeast Transformed with the Vector

Next, the present invention provides the vector comprising the polynucleotide described above. Preferably, the vector of the present invention comprises the polynucleotide (DNA) described in any one of (a) through (i) described above, the polynucleotide consisting of the nucleotide sequence of SEQ ID NO: 1 or the polynucleotide encoding the protein consisting of the amino acid sequence of SEQ ID NO: 2. The vector of the present invention is usually so constructed that the vector comprises (x) a promoter capable of transcription in yeast cells, (y) the polynucleotide (DNA) described above linked to the promoter in a sense direction or antisense direction and (z) an expression cassette comprising as the constituting element a signal that functions in yeast with respect to the transcription termination and polyadenylation of RNA molecules. When the protein of the present invention is highly expressed, it is preferred to introduce the polynucleotide (DNA) described in any one of (a) through (i) described above in a sense direction relative to the promoter so as to enhance expression of these polynucleotides.

Figure 10:
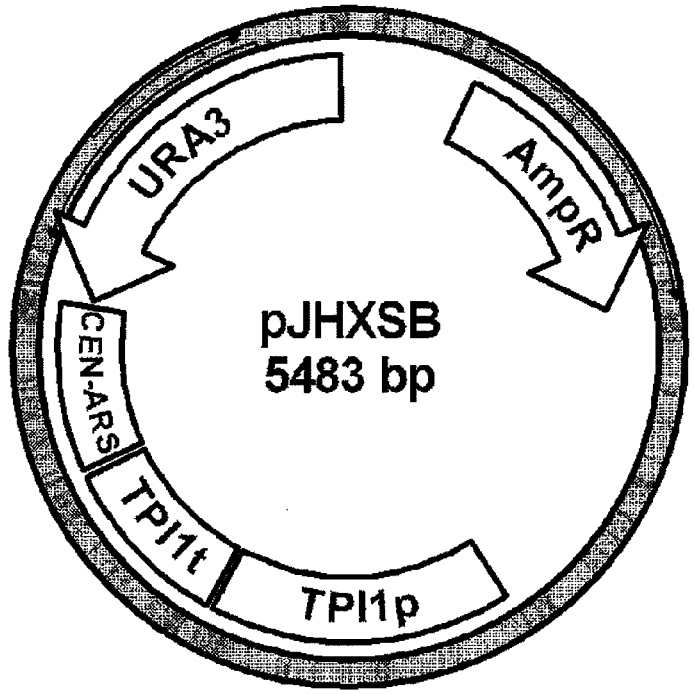
FIG. 10 shows the construction of plasmid pJHXSB.

As the vector used to introduce into the yeast, any of multicopy (YEp type), single-copy (YCp type) and chromosomal integration (YIp type) plasmids are available. For example, YEp24 (J. R. Broach et al., Experimental Manipulation of Gene Expression, Academic Press, New York, 83, 1983) is known as the YEp type vector; YCp50 (M. D. Rose et al., gene, 60, 237, 1987) is known as the YCp type vector; and YIp5 (K. Struhl, et al., Proc. Natl. Acad. Sci. USP, 76, 1035, 1979) is known as the YIp type vector, all of which are readily available. It is also possible to use plasmids such as chromosomal integration type pUP3GLP (Omura, F. et al., FEMS Microbiol. Lett., 194, 207, 2001) (FIG. 13) or pJHIXSB (FIG. 11), single-copy replicating type pYCGPY (Kodama, Y. et al., Appl. Environ. Microbiol., 67, 3455, 2001) (FIG. 12) or pJHXSB (FIG. 10), etc.

Promoters/terminators for regulating gene expression in yeasts may be used in any optional combination as far as they function in brewing yeasts and are independent from concentrations of the components such as sugar or amino acids in a moromi mash. For example, a promoter for glyceraldehyde-3-phosphate dehydrogenase gene (TDH3), a promoter for phosphoglycerate kinase gene (PGK1), etc. can be used. These genes are already cloned and described in, e.g., M. F. Tuite, et al., EMBO J., 1, 603 (1982), and easily available by known methods. The promoters used in the expression vector can be effectively replaced into those having a suitable transcription activity depending on the sugar components or sugar concentrations of moromi mash or by combining a plurality of transporters, etc.

Since any auxotrophic marker cannot be used for brewing yeasts as a selection marker used for the transformation, there are used geneticin resistant gene (G418r), copper resistant gene (CUP1) (Marin, et al., Proc. Natl. Acad. Sci. USA, Vol. 81, p 337 (1984)), cerulenin resistant gene (fas2m, PDR4) (J. Inokoshi, et al., Seikagaku, Vol. 64, p 660 (1992); Hussain, M. et al., Gene Vol. 101, p 149 (1991)), and the like. The vector constructed as described above is introduced into the host yeast.

Examples of the host yeast used in the present invention include any yeast which can be used for brewing, for example, brewing yeasts for beer, wine, sake, etc. Specifically, yeasts belonging to the genus *Saccharomyces* can be used. According to the present invention, beer yeasts, for example, *Saccharomyces* pastorianus W34/70, etc., *Saccharomyces carlsbergensis* NCYC453, NCYC456, etc., *Saccharomyces cerevisiae* NBRC1951, NBRC1952, NBRC1953, NBRC1954, etc., can be used. In addition, whisky yeasts such as *Saccharomyces cerevisiae* NCYC90, etc., wine yeasts such as wine yeast Nos. 1, 3, 4, etc. from the Brewing Society of Japan, and sake yeasts such as sake yeast Nos. 7, 9, etc. from the Brewing Society of Japan can also be used but there is no limitation thereto. In the present invention, preferably used are beer yeasts, e.g., *Saccharomyces pastorianus*.

Chromosomal DNAs used to prepare the respective transporter genes described herein are not limited to strains such as *Saccharomyces cerevisiae* ATCC 20598, ATCC 96955, etc., and may be prepared from any yeast so long as they are yeast bearing such genes and belonging to *Saccharomyces cerevisiae*.

For the yeast transformation, there can be used publicly known methods generally used. The methods that can be used for transformation include, but not limited to, an electroporation method (Meth. Enzym., 194, 182 (1990)), a spheroplast method (Proc. Natl. Acad. Sci. USA, 75, 1929 (1978)), the lithium acetate method (J. Bacteriology, 153, 163 (1983)), and methods described in Proc. Natl. Acad. Sci. USA, 75, 1929 (1978), Methods in Yeast Genetics, 2000 Edition: A Cold Spring Harbor Laboratory Course Manual, and the like.

The transformants can be selected in a uracil-free agar medium by incorporating a gene complementing a host auxotrophy such as URA3 into an expression plasmid. Alternatively, by incorporating a drug resistant gene, for example, drug resistant gene YAP1 against cycloheximide or geneticin resistant gene G418R into the expression plasmid, the transformants can be selected on a medium containing cycloheximide (e.g., 0.3 μg/ml) or geneticin (e.g., 300 μg/ml).

More specifically, a host yeast is cultured to reach an OD600 value between 1 and 6 in a standard yeast nutrition medium (e.g., YEPD medium: Genetic Engineering, Vol. 1, Plenum Press, New York, 117 (1979)), etc.). This culture yeast is collected by centrifugation, washed and pre-treated with an alkali metal ion, preferably a lithium ion, at a concentration of approximately 1 to 2 M. After the cells are allowed to stand at about 30° C. for about 60 minutes, it is allowed to stand with a DNA to be introduced (about 1 to 20 μg) at about 30° C. for about further 60 minutes. Polyethylene glycol, preferably polyethylene glycol of about 4,000 daltons, is added to reach the final concentration of about 20% to 50%. After allowing to stand at about 30° C. for about 30 minutes, the cells are heat-treated at about 42° C. for about 5 minutes. Preferably, this cell suspension is washed with a standard yeast nutrition medium, added to a predetermined amount of fresh standard yeast nutrition medium and allowed to stand at about 30° C. for about 60 minutes. Thereafter, it is spreaded onto a standard agar medium supplemented with an antibiotic or the like used as a selection marker to obtain the transformant.

Other general cloning techniques can be found in, for example, Molecular Cloning, 3rd Ed., Methods in Yeast Genetics, A laboratory manual (Cold Spring Harbor Laboratory Press, Cold Spring Harbor, N.Y.), etc.

4. Method of Producing Alcoholic Beverages of the Invention and Alcoholic Beverages Produced by the Method The vector of the present invention described above is introduced into a yeast suitable for brewing a target alcoholic beverage. Using this yeast, an alcoholic beverage having a characteristic amino acid composition can be produced. The target alcoholic beverages include, for example, but not limited to, beer, wine, whisky, sake and the like.

In producing these alcoholic beverages, known techniques can be used except that the brewing yeast obtained in the present invention is used in place of its parent strain. Accordingly, raw materials, manufacturing facilities, manufacturing control, etc. may be exactly the same as those used for the known methods and there is no increase in the cost of producing alcoholic beverages whose fermentation period is shortened. Thus, according to the present invention, alcoholic beverages can be produced using existing facilities without increasing costs.

5. Method of Assessing the Yeast of the Invention

The method involves constructing an expression vector bearing the polynucleotide obtained, introducing the vector into a yeast in a conventional manner and culturing the gene-transfected yeast in an oligosaccharide medium (e.g., a maltose/maltotriose medium). The aptitude of yeast can be evaluated by measuring the resistance to glucose-induced inactivation/degradation of the transporter contained in the yeast, the oligosaccharide assimilability, growth rate and fermentation rate of the yeast in wort, etc during its incubation. The resistance to glucose-induced inactivation/degradation, oligosaccharide assimilability, growth rate, fermentation rate in wort, etc. can be assessed by the methods used in EXAMPLES later described.

EXAMPLES

Hereinafter, the present invention will be described in more detail with reference to EXAMPLES but is not deemed to be limited thereto.

Testing Methods:

Test items and testing methods used in EXAMPLES are shown below. The testing methods in EXAMPLES were performed basically in accordance with the methods below, unless otherwise indicated.

<Acquisition of the MAL61, MAL31 and MAL21 Genes>

The MAL61 and MAL31 genes of yeast *Saccharomyces cerevisiae* were already cloned and their nucleotide sequences were reported. MAL31 (SEQ ID NO: 3) used in the specification was obtained from the *Saccharomyces* Genome Database Accession No. YBR298c and MAL61 (SEQ ID NO: 5) from the GenBank Accession No. X17391. The MAL61 and MAL31 genes were obtained by amplifying the MAL61 and MAL31 genes by PCR using as a PCR temperate chromosomal DNAs bearing the respective genes prepared from yeast *Saccharomyces cerevisiae* based on information of their nucleotide sequences and isolating the genes.

MAL21 of yeast *Saccharomyces cerevisiae* was known to be encoded by chromosome III but its DNA sequence was unknown. Taking into account that MAL31 encoded by chromosome II and the MAL61 gene encoded by chromosome VIII have the identity of 99% or more, however, it was expected that MAL21 would have a considerably high identity.

In fact, the inventors designed primers (5'AGAGCTCAG-CATATAAAGAGACA 3' (SEQ ID NO: 7) and 5'TGGATC-CGTATCTACCTACTGG 3' (SEQ ID NO: 8)) based on the DNA sequence of MAL61 obtained from GENBANK Accession No. X17391. Using as a template chromosomal DNA of yeast bearing the MAL21 gene but having no other α-glucoside transporter gene, MAL21 could be obtained by PCR. Specifically, MAL31, MAL21 and MAL61 were obtained by PCR from *Saccharomyces cerevisiae* S288C (ATCC 204508 (Rose, M. D., Winston, F. and Hieter, P., (1990), Methods in Yeast Genetics: A Laboratory Course Manual, Cold Spring Harbor Laboratory Press, Cold Spring Harbor, N.Y.), *Saccharomyces cerevisiae* ATCC 20598 and *Saccharomyces cerevisiae* ATCC 96955, respectively, using the same primers. The DNA fragments obtained were inserted into vector pCR (registered trademark) 2.1-TOPO using TOPO TA cloning kit from Invitrogen Inc., followed b DNA sequencing to confirm the inserted gene sequences.

It was confirmed that MAL31 and MAL61 were identical with the sequences registered in the data banks (Saccharomyces Genome Database Accession No. YBR298c and GenBank Accession No. X17391, respectively). For MAL21, the sequence was determined by independently sequencing 10 clones or more (SEQ ID NO: 1).

The primers used contain the XbaI or SacI site upstream of the initiation codon and the BamHI site downstream of the termination codon, which are to be incorporated into an expression vector. Amplification of the target gene by PCR using a chromosomal DNA and the following isolation can be performed by methods well known to those skilled in the art, including the preparation of PCR primers. The nucleotide sequence and amino acid sequence of MAL21 are shown in FIG. 2 and FIG. 3, respectively.

<Expression Plasmid/Plasmid for Library Construction>

In the present invention, the four expression vectors (1) to (4) were used.

(1) pJHXSB (FIG. 10)
(2) pJHIXSB (FIG. 11)
(3) pYCGPY (FIG. 12)
(4) pUP3GLP (FIG. 13)<

<Yeast Strains>

In the present invention, the strains (1) to (5) were used for acquisition of the transporter genes and for comparison among the strains, and the strains (6) to (8) were used to confirm the growth rate and fermentation rate in strains with the transporters highly expressed.

(1) *S. cerevisiae* S288C (ATCC 204508) (MATalpha SUC2 mal mel gal2 CUP1)
(2) *S. cerevisiae* ATCC 96955 (MATa MAL61 MAL62 MAL63 mal64 mal11 MAL12 mal13 ura3-52 leu2-3 leu2-112 trp1 his)
(3) *S. cerevisiae* ATCC 20598 (MATa suc MAL2 MEL1 his4 leu2)
(4) *S. cerevisiae* CB11 (Berkley Stock Center) (MATa ade1 MAL61 MAL62 MAL63 AGT1 MAL12 MAL31 MAL32)
(5) *S. cerevisiae* 111-11001 (MATa SUC2 mal mel gal2 CUP1 TPI1::TPI1pr-MAL32-G418R ura3)
(6) *S. cerevisiae* Δ152MS (MATa mal61::TRP1 MAL62 MAL63 mal64 mal11 MAL12 mal13 leu2-3 leu2-112 his URA3::TDH3p::MAL62)
(7) Top-fermenting beer yeast: AH135
(8) Bottom-fermenting beer yeast: Weihenstephan 194

<Assessment of Transporter Protein on the Maltose or Maltotriose Uptake Activity>

Expression of the introduced transporter gene in the transformant of a native transporter (which host is a strain carrying no α-glucoside transporter gene) can be examined by the presence or absence of growth in the minimum medium containing 3 mg/L of antimycin using 0.5% maltose or maltotriose as the only carbon source (6.7 g/L of yeast nitrogen base w/o amino acids, 5 g/L of maltose or maltotriose and 3 mg/L of antimycin). Even a strain which fails to function an α-glucoside transporter slightly grows on the minimum medium containing maltose or maltotriose as the only carbon source. However, when antimycin that is a respiration inhibitor is added, the strain cannot grow on the minimum medium containing maltose or maltotriose as the only carbon source and the function of α-glucoside transporter can be clearly confirmed. For example, one platinum loop of a test strain was taken out from a YPD plate (10 g/L of yeast extract, 20 g/L of polypeptone and 20 g/L of glucose), rinsed once in 1 ml of sterile water and then resuspended in sterile water adjusting to OD660=0.2. The cells were collected and again suspended in 1 ml of sterile water. The cell suspension was directly streaked onto a test medium containing maltose or maltotriose as the only carbon source to examine the growth thereby to confirm the maltose or maltotriose uptake activity.

<Assessment of Transporter Protein on 2-Deoxyglucose Resistance>

2-Deoxyglucose (2-DOG) is a sugar analog that is metabolized to 2-DOG-6-phosphate but not any further and cannot thus be a carbon source. However, it is known that 2-DOG induces glucose repression or glucose-induced inactivation to the same level as that of glucose. Accordingly, it is highly likely that strains growing on this plate would have α-glucoside transporters less susceptible to glucose-induced inactivation. In order to evaluate the resistance to 2-DOG, plates with maltose minimum medium (6.7 g/L of yeast nitrogen base w/o amino acids, 20 g/L of maltose and 0-2.0 mM of 2-deoxyglucose) or maltose-containing synthetic complete medium (SCM) (6.7 g/L of yeast nitrogen base w/o amino acids, 20 g/L of maltose, 20 mg/ml of adenine sulfate, 20 mg/ml of uracil, 20 mg/ml of L-tryptophan, 20 mg/ml of L-histidine hydrochloride, 20 mg/ml of L-arginine hydrochloride, 20 mg/ml of L-methionine, 30 mg/ml of L-tyrosine, 30 mg/ml of L-leucine, 30 mg/ml of L-isoleucine, 30 mg/ml of L-lysine hydrochloride, 50 mg/ml of L-phenylalanine, 100 mg/ml of L-glutamic acid, 100 mg/ml of L-aspartic acid, 150 mg/ml of L-valine, 200 mg/ml of L-threonine and 400 mg/ml of L-serine) supplemented with 0 mM-2 mM of 2-deoxyglucose (2-DOG) were prepared. A serial dilution of each transporter-expressed strain in the cell suspension at OD660=0.2 was spotted onto a test medium by 3 μl each and incubated at 30° C. for 2 or 3 days for assessment.

<Measurement of Level of the Transporter Protein Accumulated in Cells>

The level of the transporter protein accumulated in cells can be assayed by, e.g., Western blotting. For example, a test strain is harvested from 10 ml of culture broth during the logarithmic growth phase and disrupted in a lysis buffer (8 M urea, 5% (w/v) SDS, 40 mM Tris-HCl (pH 6.8), 0.1 mM EDTA, 1% β-mercaptoethanol) by stirring with glass beads to give the cell extract. A total protein sample of 60 μg was developed by SDS-gel electrophoresis and transferred onto a nitrocellulose membrane followed by Western blotting using rabbit polyclonal anti-Mal61p antibody. The rabbit polyclonal anti-Mal61p antibody was obtained as follows. The procedures involve inserting a DNA encoding the N-terminal region (Met1-Leu181) of Mal61p into the pET Expression vector (Novagen) downstream of GST tag in pET Expression vector (Novagen), transforming into *Escherichia coli* BL21 (DE3), applying a cell lysate of the transformant to a GST bind resin column and eluting the protein bound to the column. Full details are given in the manual attached to Novagen's pET Expression System, GST-Bind™ Affinity Resins (Novagen). The fused protein thus prepared was applied to SDS-PAGE to confirm the purity. Then, rabbit was immunized using the fused protein as an immunogen to obtain the polyclonal antibody. Effectiveness of the antibody was confirmed by culturing the α-glucoside transporter gene-expressed yeast strain and its host strain free of the gene in a YPM medium (10 g/L of yeast extract, 20 g/L of polypeptone and 5.0 g/L of maltose) and subjecting the cell lysate to Western blotting using this antibody according to the method described above. Positive bands consistent with the molecular weight of 68 kDa α-glucoside transporter were detected only in the yeast strain lysate in which the α-glucoside transporter gene was expressed.

<Measurement of Degradation Rate of Transporter Protein>

The strain expressing each transporter protein was inoculated into YPD followed by shaking culture at 30° C. overnight. The culture broth was inoculated into a YPM medium at OD660=1.0, shaking the cultured at 30° C. for 2.5 hours and then collected. The 60 OD660 units of cells were measured and suspended in 30 ml of a medium for degradation rate measurement (1.6 g/L of yeast nitrogen base w/o amino acids and ammonia, 20 g/L of glucose and 25 µg/L of cycloheximide) preincubated at 30° C., followed by incubation at 30° C. The cell suspension was sampled by 5 ml at an appropriate time (0, 10, 20, 30 and 40 minutes or 0, 30, 60, 90 and 120 minutes) immediately followed by centrifugation. The supernatant was discarded and the cells were frozen using an ethanol-dry ice. The transporter protein was detected from the frozen cells by the method described above and the intensity of the protein band was measured to determine the half life from its diminution rate.

<Assessment of Maltose Assimilability>

Assimilation of maltose by yeast constitutively expressing the transporter protein can be evaluated by aerobically culturing or fermenting yeast under conditions suitable for the yeast and measuring the level of maltose in a medium. Sugars can be measured by methods well known to those skilled in the art, for example, liquid chromatography using an IR detector. In the transformed yeast containing the nucleotide sequence of the present invention later described, the maltose uptake ability was improved.

Example 1

Screening of α-Glucoside Transporter Having the Resistance to Glucose-Induced Inactivation/Degradation Plates with 2% maltose-containing synthetic complete medium (SCM) supplemented with 0 mM to 2 mM of 2-deoxyglucose (2-DOG) were prepared. 2-DOG is a sugar analog that is metabolized to 2-DOG-6-phosphate but not any further and cannot thus be a carbon source. However, it is known that 2-DOG induces glucose repression or glucose-induced inactivation to the same level as glucose. It is therefore highly likely that a strain grown on this plate would have an α-glucoside transporter less susceptible to glucose-induced inactivation. In a number of yeast strains, the cell suspension was spotted, followed by incubation at 30° C. As a result, MAL21-bearing yeast strain ATCC 20598 grew even on the plate containing 1 mM of 2-DOG unlike the other strains, indicating that the strain was predictably a transporter less susceptible to glucose-induced degradation (FIG. 1). Accordingly, the primers (SEQ ID NOS: 7 and 8) were designed based on the nucleotide sequence information about 5' upstream and 3' downstream of MAL61 encoding gene. The MAL21 gene was amplified by PCR using the genomic DNA ATCC 20598 as a template and cloned into Invitrogen's pCR2.1-TOPO followed by DNA sequencing. The nucleotide sequence (SEQ ID NO: 1) and the amino acid sequence (SEQ ID NO: 2) are shown in FIGS. 2 and 3, respectively. Alignment of the amino acid sequence for Mal21p/Mal31p/Mal61p is shown in FIG. 4-1 and alignment of the nucleotide sequence of the nucleotide sequence in FIGS. 4-2 to 4-4.

Figure 5:
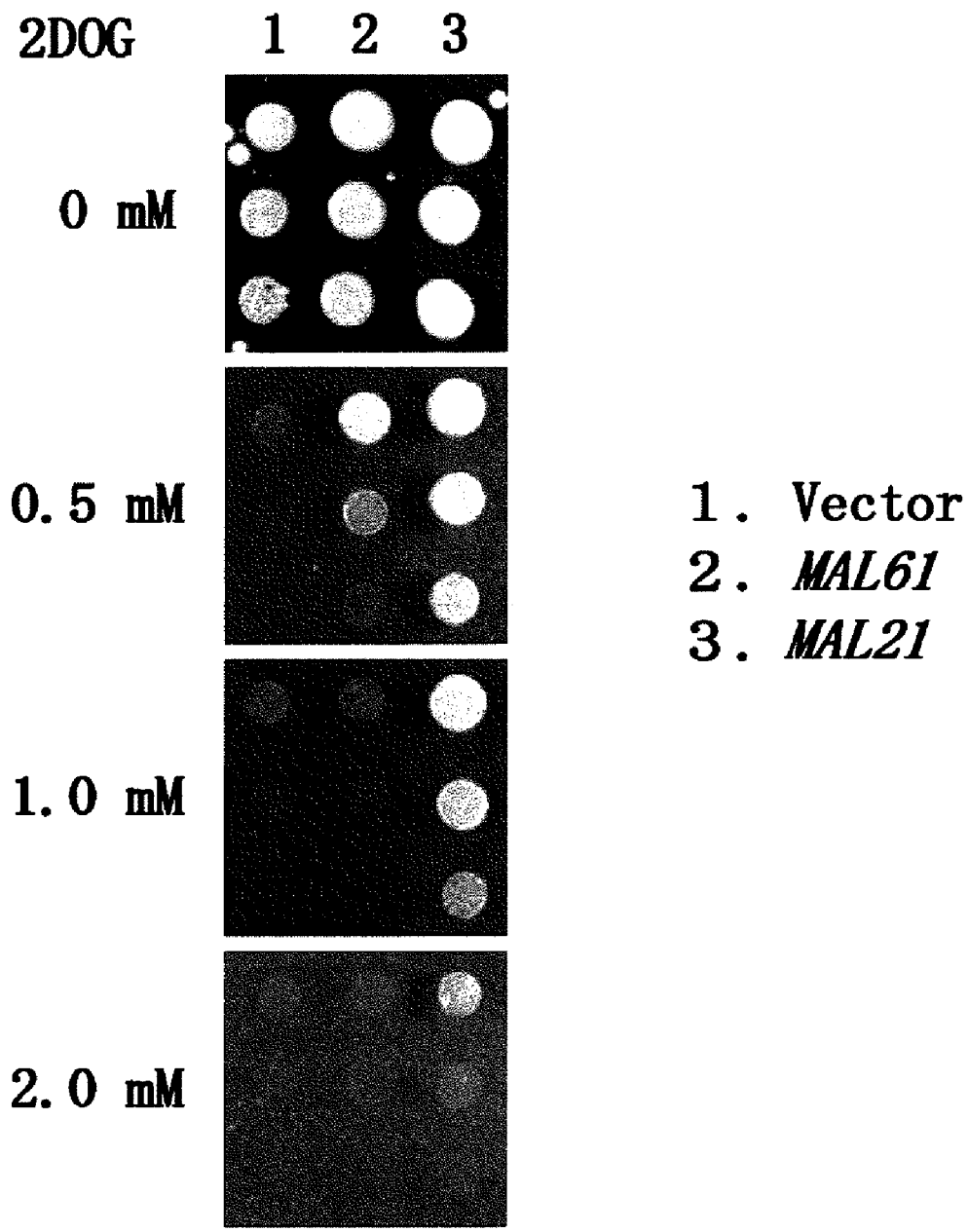
FIG. 5 shows the differences in growth among strains bearing MAL21/MAL61 gene in the presence of 2-deoxyglucose.
Figure 11:
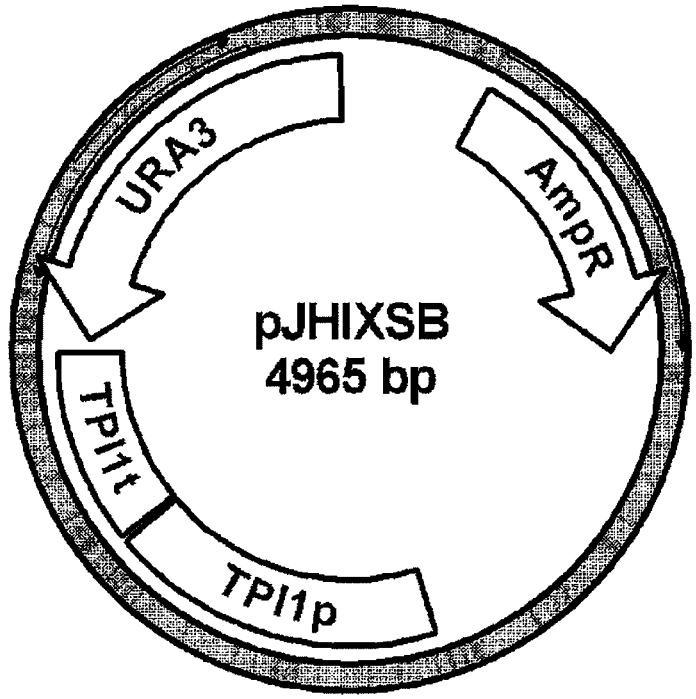
FIG. 11 shows the construction of plasmid pJHIXSB.
Figure 12:
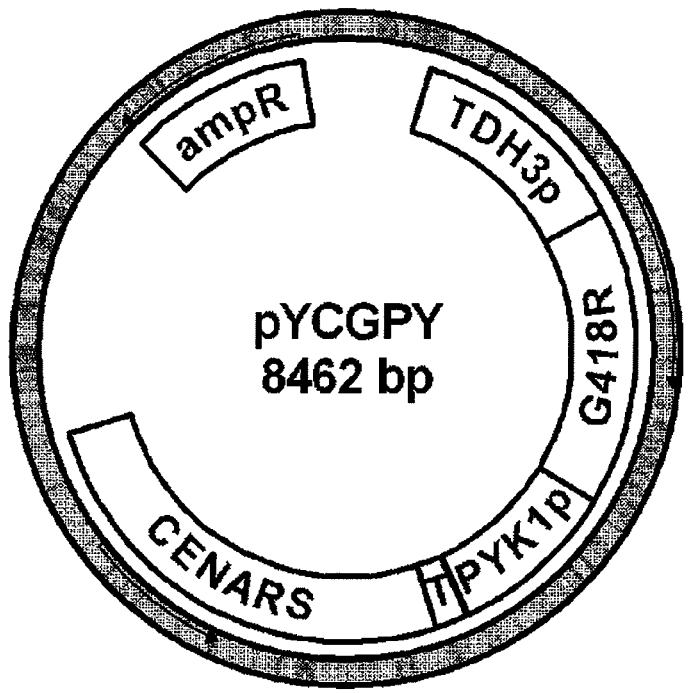
FIG. 12 shows the construction of plasmid pYCGPY.

This MAL21 gene was incorporated into the SacI-BamHI site of plasmid pJHIXSB (FIG. 11). After digesting with EcoRV in the URA3 gene, the plasmid pJHIMAL21 was incorporated into yeast HH1001 as an expression unit constitutively transcribed by the TPI1 promoter, which was named HH206 strain. HH1001 is an ura3-sibling of the mal-strain X2180-1A and constitutively expresses maltase since TPI1p::MAL32 (which encodes the maltase gene) is incorporated therein. Growth of the HH206 strain was examined by applying the strain onto SCM plates containing 0 mM to 2 mM of 2-DOG. The HH108 and HH227 strains carrying the MAL61 and MAL31 genes could not grow on the 1.0 mM 2-DOG plate, whereas the HH206 strain grew on the 2.0 mM 2-DOG plate (FIG. 5).

Figure 6:
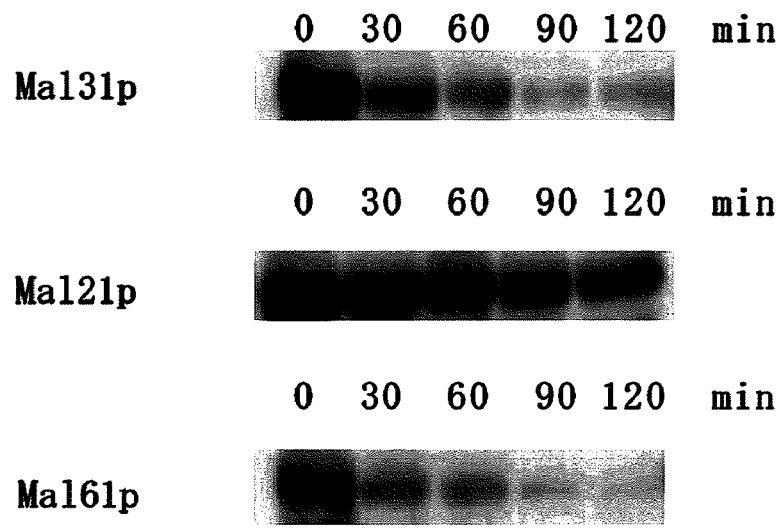
FIG. 6 shows the degradation rate of Mal21p and Mal61p in the presence of glucose.

In addition, the glucose-induced degradation rate of Mal21p was assayed by Western blotting using anti-Mal61p antibody. It was found that the half life was about 2 hours, whereas the half life of Mal31p and Mal61p was about 20 minutes. It was confirmed that Mal21p had a much longer half life than the other transporters (FIG. 6).

Example 2

Figure 7:
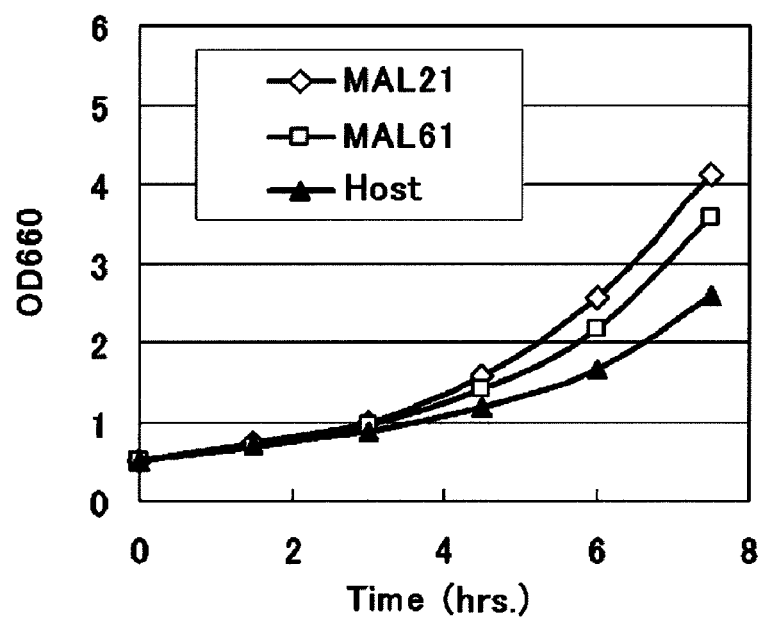
FIG. 7 shows the growth of MAL21/MAL61 gene-highly expressed laboratory strains in a maltose medium.

Growth of MAL61-Highly Expressed Strain and MAL21-Highly Expressed Strain in Maltose Medium MAL61 and MAL21 were incorporated into plasmid pYCGPY at the SacI-BamHI site downstream of the PYK1 promoter. The respective plasmids were named pYCGPY-MAL61 and pYCGPYMAL21. The plasmid pYCGPY is a YCp type plasmid bearing CEN-ARS and has a G418-resistant gene, an Ap-resistant gene, etc. (FIG. 12). pYCGPY-MAL61 and pYCGPYMAL21 were transformed into Δ152MS strain. The Δ152MS strain is a strain wherein MAL61 in ATCC 96955 is disrupted by TRP1 marker and MAL62 (maltase gene) under control of the TDH3 promoter is introduced. Δ152MS (pYCGPYMAL61) and Δ152MS (pYCGPYMAL21) were inoculated into YPM (10 g/L or yeast extract, 20 g/L or polypeptone and 5.0 g/L of maltose) to have OD660=about 0.5, followed by shake culture at 30° C. The OD660 data was monitored every 1.5 hour (FIG. 7). Δ152MS (pYCGPYMAL21) grew more rapidly in maltose than Δ152MS (pYCGPYMAL61), and effects of the transporters having the resistance to glucose-induced degradation were confirmed in the laboratory strains.

Example 3

Figure 13:
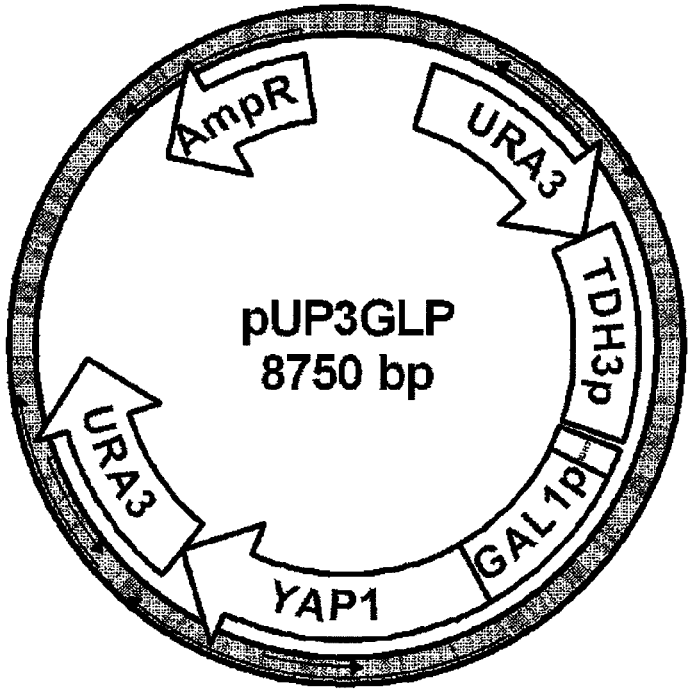
FIG. 13 shows the construction of plasmid pUP3GLP.

Test on Happoshu (Low-Malt Beer) Wort Fermentation by Bottom-Fermenting Beer Yeast where MAL21 was Expressed at High Level The transporter MAL21 having the resistance to glucose-induced degradation was incorporated into plasmid pUP3GLP at the XbaI (or SacI)-BamHI site. pUP3GLP is shown in FIG. 13. pUP3GLP is a YIp type plasmid, in which the transporter gene is expressed from glyceraldehyde triphosphate dehydrogenase promoter (TDH3p). After each plasmid was digested at the EcoRV site in URA3, the digestion product was transformed into bottom-fermenting beer yeast (Weihenstephan 194) and the transformant was spread onto a YGP plate (10 g/L of yeast extract, 20 g/L of polypeptone and 20 g/L of galactose) supplemented with 0.3 µg/ml of cycloheximide. The objective expression cassette was inserted into the URA3 gene on the chromosome of Weihenstephan 194, which was confirmed by PCR.

Figure 8:
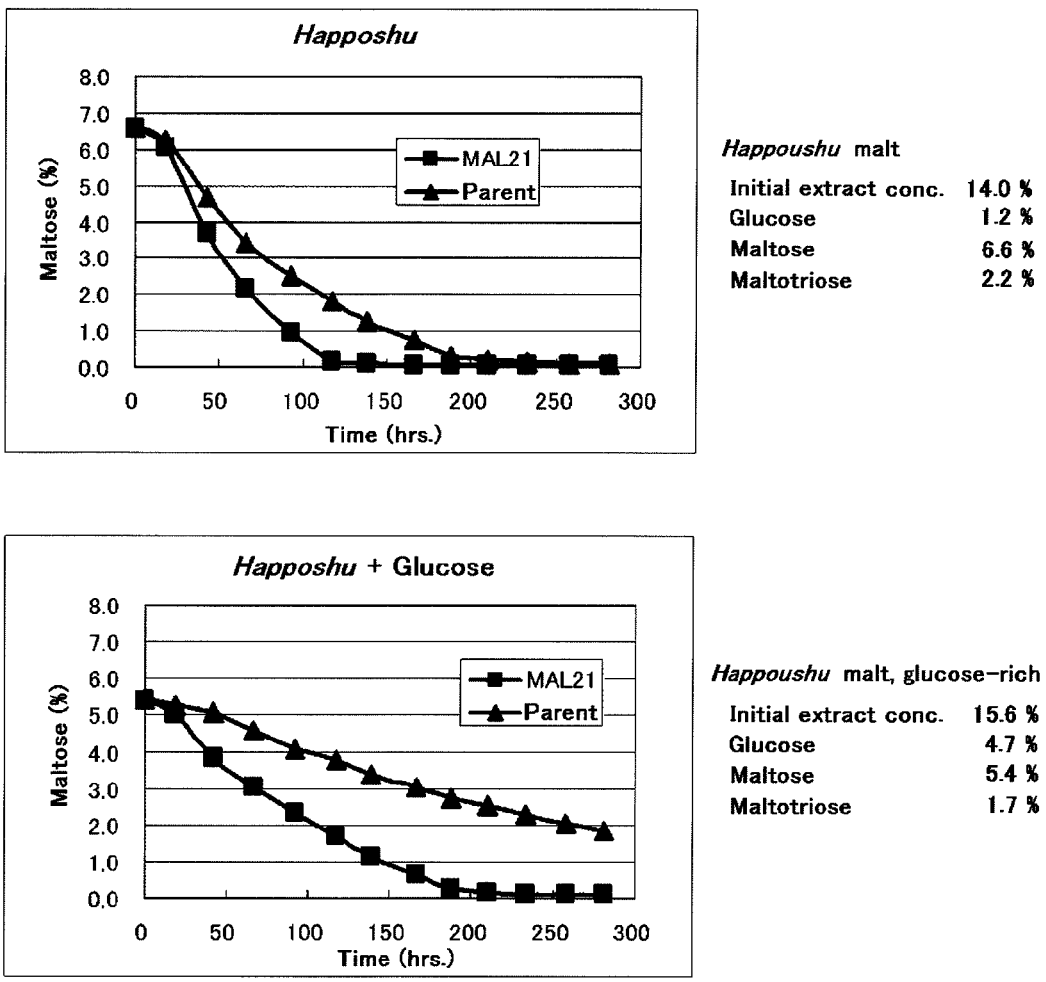
FIG. 8 shows the maltose fermentation rates of MAL21 gene-highly expressed bottom-fermenting beer yeast strains in happoshu (low-malt beer) or in happoshu (glucose-rich) wort.

Weihenstephan 194 (URA3::TDH3p::MAL21) and parent strain Weihenstephan 194 were inoculated into two kinds of happoshu wort. The happoshu wort is a wort with less than 25% malt content in the raw materials except for water, in which glycosylated starch, hops, etc. are used. One of the worts for happoshu has an initial extract concentration of 14.0% and contains sugars in proportions of 1.2% of glucose, 6.6% of maltose and 2.2% of maltotriose. Another glucose-rich happoshu wort has an initial extract concentration of 15.6% and contains sugars in proportions of 4.7% of glucose, 5.4% of maltose and 1.7% of maltotriose. Each wort was prepared by adding glycosylated starch having different sugar proportions to the same volume of wort (final concentration, less than 25% malt content). Wet cells were pitched into each wort to become 7.5 g/L, which was allowed to ferment at 15° C. The maltose content in the moromi mash during the fermentation was measured. The results are shown in FIG. 8.

In any happoshu wort, the assimilation rate of maltose in the MAL21-highly expressed strains was markedly faster than in the parent strain Weihenstephan 194. Especially in the glucose-rich happoshu wort, its effect was remarkable. The high initial extract concentration means that the glucose content is high and the effect of the transporter having the resistance to glucose-induced degradation was fully observed.

Example 4

Figure 9:
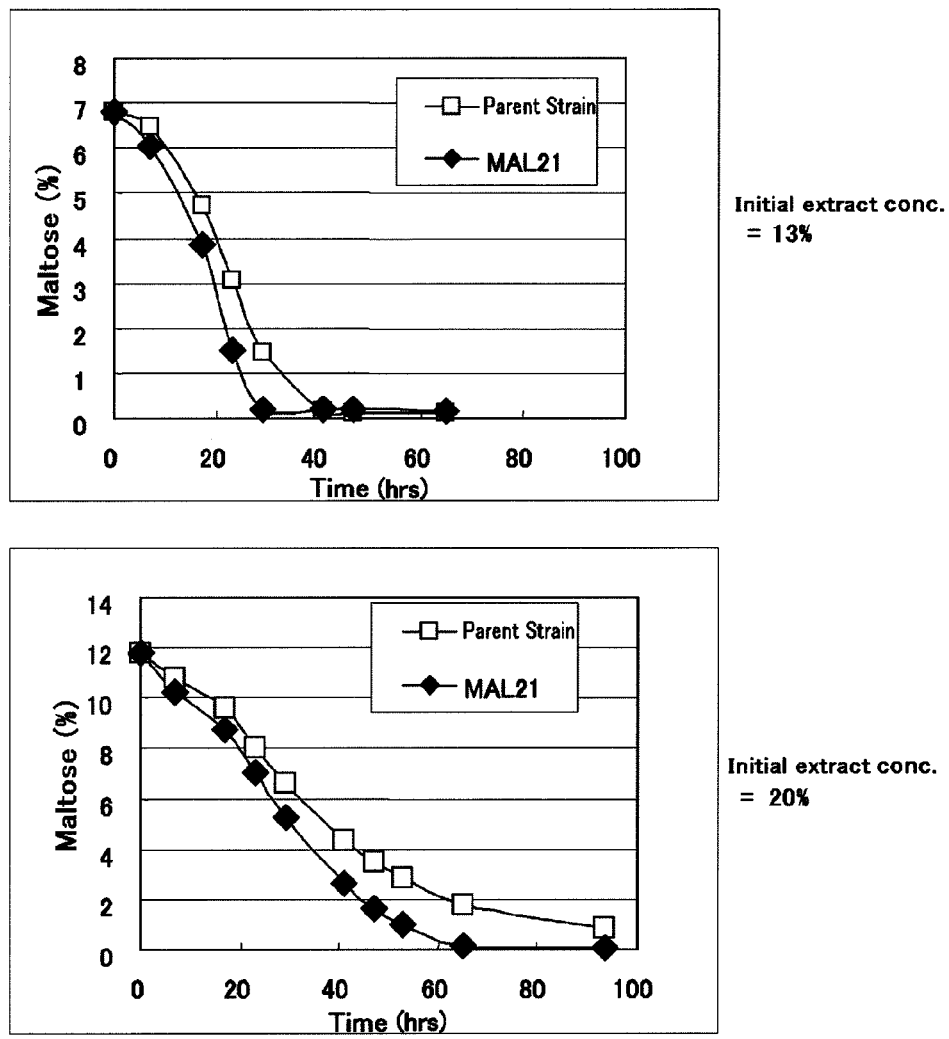
FIG. 9 shows the maltose fermentation rates in the wort of top-fermenting beer yeasts in which the Mal21p transporter is highly expressed.

Wort Fermentation Test by Top-Fermenting Beer Yeast in which MAL21 was Highly Expressed Glucose-induced degradation-resistant transporter MAL21 was incorporated into plasmid pUP3GLP at the XbaI (or SacI)-BamHI site. pUP3GLP is shown in FIG. 13. pUP3GLP is a YIp plasmid and the transporter gene is expressed by glyceraldehyde triphosphate dehydrogenase promoter (TDH3p). After each plasmid was digested at the EcoRV site in URA3, the digestion product was transformed into top-fermenting yeast AH135 and the transformant was spread onto a YPG plate (10 g/L of yeast extract, 20 g/L of polypeptone and 20 g/L of galactose) supplemented with 0.3 µg/ml of cycloheximide. It was confirmed by PCR that the objective expression cassette was inserted into the URA3 gene on the chromosome of AH135. AH135 (URA3::TDH3p::MAL21) was pitched into a 100% malt wort with an initial extract concentration of 13% or 20% containing as the initial extract concentration adjusted to 5 g/L of wet cells. Fermentation was conducted at 15° C. and the maltose concentration in the mash during fermentation was measured. The results are shown in FIG. 9.

The maltose assimilation rate was faster than the parent strain AH135 even using either strain. Especially in the initial extract concentration of 20%, its effect was remarkable. The initial extract concentration being high indicates that the glucose concentration is high, meaning that the transporter having the resistance to glucose-induced degradation was effective. It was confirmed that the high level expression of the transporter having the resistance to glucose-induced degradation was effective not only for the bottom-fermenting beer yeast but also for top-fermenting beer yeast.

As described above, it has been found that Mal21p naturally present in some yeasts is less susceptible to glucose-induced degradation, unlike other α-glucoside transporters. It has also been confirmed that assimilation of sugars such as maltose in mash, etc. taken up by the transporter can be accelerated by using yeasts (irrespective of laboratory strains or brewing yeasts) capable of expressing the transporter. Especially when the concentration of monosaccharides such as glucose is high, the effects are more prominent.

INDUSTRIAL APPLICABILITY

The yeast bearing the transporter in accordance with the present invention which has the resistance to glucose-induced inactivation/degradation provides improved oligosaccharide assimilability and is excellent in its ability to assimilate sugars such as maltose, etc. Such yeast can be effectively used in brewing beer or wine.

The invention claimed is:

1. An isolated polynucleotide selected from the group consisting of (a) to (c) below:
  (a) a polynucleotide comprising the nucleotide sequence of SEQ ID NO: 1;
  (b) a polynucleotide comprising a nucleotide sequence encoding a protein consisting of the amino acid sequence of SEQ ID NO: 2; and
  (c) a polynucleotide comprising a nucleotide sequence encoding an α-glucoside transporter protein comprising an amino acid sequence having an identity of at least 99.1% with the amino acid sequence of SEQ ID NO: 2, wherein said α-glucoside transporter protein has a resistance to glucose-induced inactivation and/or degradation, and said a-glucoside transporter protein has maltose or maltotriose uptake activity.

2. The isolated polynucleotide according to claim 1, wherein said polynucleotide comprising a nucleotide sequence encoding an α-glucoside transporter protein comprising an amino acid sequence having an identity of at least 99.5% with the amino acid sequence of SEQ ID NO: 2.

3. The isolated polynucleotide according to claim 1, wherein said polynucleotide comprising the nucleotide sequence of SEQ ID NO: 1.

4. The isolated polynucleotide according to claim 1, wherein said polynucleotide comprising a nucleotide sequence encoding a protein consisting of the amino acid sequence of SEQ ID NO: 2.

5. The polynucleotide according to claim 1, which is a DNA.

6. A vector comprising the polynucleotide according to claim 1.

7. A yeast transfected with the vector according to claim 6.

8. The yeast according to claim 7, wherein the vector is an expression vector.

9. A yeast transfected with a vector comprising a polynucleotide, wherein oligosaccharide assimilability of said yeast is enhanced by expression of said polynucleotide, wherein said polynucleotide is selected from the group consisting of (a) to (c) below:
  (a) a polynucleotide comprising the nucleotide sequence of SEQ ID NO: 1;
  (b) a polynucleotide comprising a nucleotide sequence encoding a protein consisting of the amino acid sequence of SEQ ID NO: 2; and
  (c) a polynucleotide comprising a nucleotide sequence encoding an α-glucoside transporter protein comprising an amino acid sequence having an identity of at least 99.1% with the amino acid sequence of SEQ ID NO: 2, wherein said α-glucoside transporter protein has a resistance to glucose-induced inactivation and/or degradation, and said α-glucoside transporter protein has maltose or maltotriose uptake activity.

* * * * *